(12) United States Patent
Yampolsky et al.

(10) Patent No.: US 11,617,627 B2
(45) Date of Patent: Apr. 4, 2023

(54) SYSTEMS AND METHODS FOR OPTICAL STRAIN SENSING IN MEDICAL INSTRUMENTS

(71) Applicant: Auris Health, Inc., Redwood City, CA (US)

(72) Inventors: Steven E. Yampolsky, Oakland, CA (US); Enrique Romo, Danville, CA (US)

(73) Assignee: Auris Health, Inc., Redwood City, CA (US)

( * ) Notice: Subject to any disclaimer, the term of this patent is extended or adjusted under 35 U.S.C. 154(b) by 446 days.

(21) Appl. No.: 16/828,370

(22) Filed: Mar. 24, 2020

(65) Prior Publication Data

US 2020/0305983 A1    Oct. 1, 2020

Related U.S. Application Data

(60) Provisional application No. 62/826,825, filed on Mar. 29, 2019.

(51) Int. Cl.
*A61B 34/00*   (2016.01)
*A61B 34/37*   (2016.01)
(Continued)

(52) U.S. Cl.
CPC ............. *A61B 34/71* (2016.02); *A61B 34/37* (2016.02); *A61B 2034/2061* (2016.02); *A61B 2034/301* (2016.02); *A61B 2090/064* (2016.02)

(58) Field of Classification Search
CPC . A61B 34/71; A61B 34/37; A61B 2034/2061; A61B 2034/301; A61B 2090/064; A61B 34/25; A61B 34/20; A61B 2017/00477; A61B 2017/00809; A61B 2034/105; A61B 2034/2051; A61B 2034/2065; A61B 2090/306; A61B 2090/309; A61B 2090/3614; A61B 2090/376; A61B 2217/005; A61B 2217/007; A61G 13/02; A61G 13/04; A61G 13/06; A61G 13/08; A61G 13/107
See application file for complete search history.

(56) References Cited

U.S. PATENT DOCUMENTS 3,572,325 A    3/1971    Bazell et al.
3,913,565 A    10/1975    Kawahara
(Continued)

FOREIGN PATENT DOCUMENTS

CN    1846181    10/2006
CN    1857877    11/2006
(Continued)

*Primary Examiner* — Joseph M Dietrich
*Assistant Examiner* — Michael T. Holtzclaw
(74) *Attorney, Agent, or Firm* — Chang & Hale LLP

(57) ABSTRACT

Certain aspects relate to systems and techniques for optical strain sensing in medical instruments. In one aspect, a medical instrument includes an elongated shaft, and at least one pull wire extending from a proximal end of the elongated shaft to the distal end of the elongated shaft. The at least one pull wire is configured to cause actuation of the medical instrument in at least one degree of freedom. The at least one pull wire includes an optical fiber configured to provide an indication of strain along the at least one pull wire.

30 Claims, 27 Drawing Sheets

(51) Int. Cl.
 *A61B 34/30* (2016.01)
 *A61B 34/20* (2016.01)
 *A61B 90/00* (2016.01)

(56) References Cited

U.S. PATENT DOCUMENTS

| | | | |
|---|---|---|---|
| 4,294,234 A | 10/1981 | Matsuo |
| 4,392,485 A | 7/1983 | Hiltebrandt |
| 4,607,619 A | 8/1986 | Seike et al. |
| 4,690,175 A | 9/1987 | Ouchi et al. |
| 4,706,656 A | 11/1987 | Kubota |
| 4,741,326 A | 5/1988 | Sidall et al. |
| 4,745,908 A | 5/1988 | Wardle |
| 4,748,969 A | 6/1988 | Wardle |
| 4,750,475 A | 6/1988 | Yoshihashi |
| 4,771,766 A | 9/1988 | Aoshiro |
| 4,846,791 A | 7/1989 | Hattler et al. |
| 4,869,238 A | 9/1989 | Opie et al. |
| 4,906,496 A | 3/1990 | Hosono et al. |
| 4,907,168 A | 3/1990 | Boggs |
| 4,967,732 A | 11/1990 | Inoue |
| 5,050,585 A | 9/1991 | Takahashi |
| 5,083,549 A | 1/1992 | Cho et al. |
| 5,106,387 A | 4/1992 | Kittrell et al. |
| 5,108,800 A | 4/1992 | Koo |
| 5,125,909 A | 6/1992 | Heimberger |
| 5,168,864 A | 12/1992 | Shockey |
| 5,217,002 A | 6/1993 | Katsurada |
| 5,251,611 A | 10/1993 | Zehel |
| 5,257,617 A | 11/1993 | Takahashi |
| 5,261,391 A | 11/1993 | Inoue |
| 5,287,861 A | 2/1994 | Wilk |
| 5,313,934 A | 5/1994 | Wiita et al. |
| 5,386,818 A | 2/1995 | Schneebaum |
| 5,448,988 A | 9/1995 | Watanabe |
| 5,478,330 A | 12/1995 | Imran et al. |
| 5,482,029 A | 1/1996 | Sekiguchi |
| 5,489,270 A | 2/1996 | van Erp |
| 5,507,725 A | 4/1996 | Savage et al. |
| 5,533,985 A | 7/1996 | Wang |
| 5,580,200 A | 12/1996 | Fullerton |
| 5,681,296 A | 10/1997 | Ishida |
| 5,704,534 A | 1/1998 | Huitema et al. |
| 5,720,775 A | 2/1998 | Larnard |
| 5,741,429 A | 4/1998 | Donadio, III |
| 5,749,889 A | 5/1998 | Bacich et al. |
| 5,873,817 A | 2/1999 | Kokish et al. |
| 5,876,325 A | 3/1999 | Mizuno et al. |
| 5,879,287 A | 3/1999 | Yoshihashi |
| 5,882,347 A | 3/1999 | Mouris-Laan |
| 5,888,191 A | 3/1999 | Akiba |
| 5,910,129 A | 6/1999 | Koblish et al. |
| 5,938,586 A | 8/1999 | Wilk |
| 5,938,587 A | 8/1999 | Taylor et al. |
| 6,012,494 A | 1/2000 | Balazs |
| 6,143,013 A | 11/2000 | Samson et al. |
| 6,157,853 A | 12/2000 | Blume et al. |
| 6,174,280 B1 | 1/2001 | Oneda |
| 6,197,015 B1 | 3/2001 | Wilson |
| 6,198,974 B1 | 3/2001 | Webster, Jr. |
| 6,234,958 B1 | 5/2001 | Snoke et al. |
| 6,315,715 B1 | 11/2001 | Taylor et al. |
| 6,404,497 B1 | 6/2002 | Backman |
| 6,436,107 B1 | 8/2002 | Wang et al. |
| 6,464,632 B1 | 10/2002 | Taylor |
| 6,485,411 B1 | 11/2002 | Konstorum |
| 6,491,626 B1 | 12/2002 | Stone et al. |
| 6,537,205 B1 | 3/2003 | Smith |
| 6,554,793 B1 | 4/2003 | Pauker et al. |
| 6,716,178 B1 | 4/2004 | Kilpatrick et al. |
| 6,746,422 B1 | 6/2004 | Noriega |
| 6,749,560 B1 | 6/2004 | Konstorum |
| 6,790,173 B2 | 9/2004 | Saadat |
| 6,827,710 B1 | 12/2004 | Mooney et al. |
| 6,827,712 B2 | 12/2004 | Tovey et al. |
| 6,837,846 B2 | 1/2005 | Jaffe |
| 6,908,428 B2 | 6/2005 | Aizenfeld |
| 6,921,362 B2 | 7/2005 | Ouchi |
| 6,958,035 B2 | 10/2005 | Friedman et al. |
| 7,008,401 B2 | 3/2006 | Thompson et al. |
| 7,130,700 B2 | 10/2006 | Gardeski et al. |
| 7,594,903 B2 | 9/2009 | Webler et al. |
| 7,645,230 B2 | 1/2010 | Mikkaichi |
| 7,645,231 B2 | 1/2010 | Akiba |
| 7,789,827 B2 | 9/2010 | Landry |
| 7,930,065 B2 | 4/2011 | Larkin et al. |
| 8,046,049 B2 | 10/2011 | Govari et al. |
| 8,052,636 B2 | 11/2011 | Moll et al. |
| 8,246,536 B2 | 8/2012 | Ochi |
| 8,444,637 B2 | 5/2013 | Podmore et al. |
| 8,460,236 B2 | 6/2013 | Roelle et al. |
| 8,498,691 B2 | 7/2013 | Moll et al. |
| 8,515,215 B2 | 8/2013 | Younge et al. |
| 8,652,030 B2 | 2/2014 | Matsuura et al. |
| 8,686,747 B2 | 4/2014 | Berner |
| 8,758,231 B2 | 6/2014 | Bunch et al. |
| 8,827,947 B2 | 9/2014 | Bosman et al. |
| 8,864,655 B2 * | 10/2014 | Ramamurthy ....... A61B 5/0059 600/117 |
| 8,989,528 B2 * | 3/2015 | Udd ....... A61B 5/065 385/13 |
| 9,186,046 B2 | 11/2015 | Ramamurthy et al. |
| 9,314,953 B2 | 4/2016 | Lauer |
| 9,427,551 B2 | 8/2016 | Leeflang et al. |
| 9,504,604 B2 | 11/2016 | Alvarez |
| 9,561,083 B2 | 2/2017 | Yu et al. |
| 9,591,990 B2 | 3/2017 | Chen et al. |
| 9,622,827 B2 | 4/2017 | Yu et al. |
| 9,636,184 B2 | 5/2017 | Lee et al. |
| 9,713,509 B2 | 7/2017 | Schuh et al. |
| 9,727,963 B2 | 8/2017 | Mintz et al. |
| 9,737,371 B2 | 8/2017 | Romo et al. |
| 9,737,373 B2 | 8/2017 | Schuh |
| 9,744,335 B2 | 8/2017 | Jiang |
| 9,763,741 B2 | 9/2017 | Alvarez et al. |
| 9,788,910 B2 | 10/2017 | Schuh |
| 9,795,505 B2 * | 10/2017 | Yu ....... A61F 9/00736 |
| 9,844,353 B2 | 12/2017 | Walker et al. |
| 9,844,412 B2 | 12/2017 | Bogusky et al. |
| 9,867,635 B2 | 1/2018 | Alvarez et al. |
| 9,918,659 B2 | 3/2018 | Chopra |
| 9,918,681 B2 | 3/2018 | Wallace et al. |
| 9,931,025 B1 | 4/2018 | Graetzel et al. |
| 9,949,749 B2 | 4/2018 | Noonan et al. |
| 9,955,986 B2 | 5/2018 | Shah |
| 9,962,228 B2 | 5/2018 | Schuh et al. |
| 9,980,785 B2 | 5/2018 | Schuh |
| 9,993,313 B2 | 6/2018 | Schuh et al. |
| 10,016,900 B1 | 7/2018 | Meyer et al. |
| 10,022,192 B1 | 7/2018 | Ummalaneni |
| 10,080,576 B2 | 9/2018 | Romo et al. |
| 10,130,427 B2 | 11/2018 | Tanner et al. |
| 10,136,959 B2 | 11/2018 | Mintz et al. |
| 10,145,747 B1 | 12/2018 | Lin et al. |
| 10,149,720 B2 | 12/2018 | Romo |
| 10,159,532 B1 | 12/2018 | Ummalaneni et al. |
| 10,159,533 B2 | 12/2018 | Moll et al. |
| 10,169,875 B2 | 1/2019 | Mintz et al. |
| 10,219,874 B2 | 3/2019 | Yu et al. |
| 10,231,793 B2 | 3/2019 | Romo |
| 10,231,867 B2 | 3/2019 | Alvarez et al. |
| 10,244,926 B2 | 4/2019 | Noonan et al. |
| 10,285,574 B2 | 5/2019 | Landey et al. |
| 10,299,870 B2 | 5/2019 | Connolly et al. |
| 10,314,463 B2 | 6/2019 | Agrawal et al. |
| 10,363,103 B2 | 7/2019 | Alvarez et al. |
| 10,376,672 B2 | 8/2019 | Yu |
| 10,383,765 B2 | 8/2019 | Alvarez et al. |
| 10,398,518 B2 | 9/2019 | Yu et al. |
| 10,405,939 B2 | 9/2019 | Romo et al. |
| 10,405,940 B2 | 9/2019 | Romo |
| 10,426,559 B2 | 10/2019 | Graetzel et al. |
| 10,426,661 B2 | 10/2019 | Kintz |
| 10,434,660 B2 | 10/2019 | Meyer |

(56) References Cited

U.S. PATENT DOCUMENTS

| | | |
|---|---|---|
| 10,463,439 B2 | 11/2019 | Joseph et al. |
| 10,464,209 B2 | 11/2019 | Ho et al. |
| 10,470,830 B2 | 11/2019 | Hili |
| 10,482,599 B2 | 11/2019 | Mintz et al. |
| 10,493,241 B2 | 12/2019 | Jiang |
| 10,500,001 B2 | 12/2019 | Yu et al. |
| 10,517,692 B2 | 12/2019 | Eyre et al. |
| 10,524,866 B2 | 1/2020 | Srinivasan |
| 10,539,478 B2 | 1/2020 | Lin |
| 10,543,048 B2 | 1/2020 | Noonan et al. |
| 10,555,778 B2 | 2/2020 | Ummalaneni et al. |
| 10,555,780 B2 | 2/2020 | Tanner et al. |
| 10,765,487 B2 | 9/2020 | Ho |
| 2001/0004676 A1 | 6/2001 | Ouchi |
| 2003/0036748 A1 | 2/2003 | Cooper et al. |
| 2003/0130564 A1 | 7/2003 | Martone et al. |
| 2003/0158545 A1 | 8/2003 | Hovda et al. |
| 2003/0163199 A1 | 8/2003 | Chu et al. |
| 2003/0195664 A1 | 10/2003 | Nowlin et al. |
| 2004/0015122 A1 | 1/2004 | Zhang et al. |
| 2004/0054322 A1 | 3/2004 | Vargas |
| 2004/0072066 A1 | 4/2004 | Cho et al. |
| 2004/0138525 A1 | 7/2004 | Saadat et al. |
| 2004/0193013 A1 | 9/2004 | Isakawa et al. |
| 2004/0249246 A1 | 12/2004 | Campos |
| 2005/0004515 A1 | 1/2005 | Hart et al. |
| 2005/0125005 A1 | 6/2005 | Fujikura |
| 2005/0131279 A1 | 6/2005 | Boulais et al. |
| 2005/0154262 A1 | 7/2005 | Banik et al. |
| 2005/0159646 A1 | 7/2005 | Nordstrom et al. |
| 2005/0165366 A1 | 7/2005 | Brustad |
| 2005/0222581 A1 | 10/2005 | Fischer et al. |
| 2005/0234293 A1 | 10/2005 | Yamamoto |
| 2005/0256452 A1 | 11/2005 | DeMarchi |
| 2005/0272975 A1 | 12/2005 | McWeeney et al. |
| 2005/0273085 A1 | 12/2005 | Hinman et al. |
| 2005/0288549 A1 | 12/2005 | Mathis |
| 2006/0013523 A1* | 1/2006 | Chiidlers ............ G02B 6/02042 |
| | | 385/12 |
| 2006/0041188 A1 | 2/2006 | Dirusso et al. |
| 2006/0111692 A1 | 5/2006 | Hlavka et al. |
| 2006/0241368 A1 | 10/2006 | Fichtinger et al. |
| 2006/0264708 A1 | 11/2006 | Horne |
| 2006/0276827 A1 | 12/2006 | Mitelberg et al. |
| 2007/0060879 A1 | 3/2007 | Weilzner et al. |
| 2007/0112355 A1 | 5/2007 | Salahieh |
| 2007/0135733 A1 | 6/2007 | Soukup et al. |
| 2007/0135763 A1 | 6/2007 | Musbach et al. |
| 2007/0135803 A1 | 6/2007 | Belson |
| 2007/0156019 A1 | 7/2007 | Larkin et al. |
| 2007/0270645 A1 | 11/2007 | Ikeda |
| 2007/0270679 A1 | 11/2007 | Nguyen et al. |
| 2007/0282167 A1 | 12/2007 | Barenboym et al. |
| 2007/0287886 A1 | 12/2007 | Saadat |
| 2008/0039255 A1 | 2/2008 | Jinno et al. |
| 2008/0051629 A1 | 2/2008 | Sugiyama et al. |
| 2008/0065103 A1 | 3/2008 | Cooper et al. |
| 2008/0097293 A1 | 4/2008 | Chin et al. |
| 2008/0108869 A1 | 5/2008 | Sanders et al. |
| 2008/0139887 A1 | 6/2008 | Fitpatrick |
| 2008/0146874 A1 | 6/2008 | Miller |
| 2008/0147089 A1 | 6/2008 | Loh |
| 2008/0177285 A1 | 7/2008 | Brock et al. |
| 2008/0208001 A1 | 8/2008 | Hadani |
| 2008/0212082 A1 | 9/2008 | Froggatt et al. |
| 2008/0218770 A1 | 9/2008 | Moll et al. |
| 2009/0099420 A1 | 4/2009 | Woodley et al. |
| 2009/0163851 A1 | 6/2009 | Holloway |
| 2009/0247880 A1 | 10/2009 | Naruse et al. |
| 2009/0254083 A1 | 10/2009 | Wallace et al. |
| 2009/0299344 A1 | 12/2009 | Lee et al. |
| 2009/0306587 A1 | 12/2009 | Milijasevic et al. |
| 2009/0324161 A1* | 12/2009 | Prisco .................... G01L 1/246 |
| | | 385/12 |
| 2010/0030023 A1 | 2/2010 | Yoshie |
| 2010/0073150 A1 | 3/2010 | Olson et al. |
| 2010/0114115 A1 | 5/2010 | Schlesinger et al. |
| 2010/0130823 A1 | 5/2010 | Ando |
| 2010/0168918 A1 | 7/2010 | Zhao |
| 2010/0217184 A1 | 8/2010 | Koblish et al. |
| 2010/0249497 A1 | 9/2010 | Peine et al. |
| 2010/0249506 A1 | 9/2010 | Prisco et al. |
| 2010/0250000 A1* | 9/2010 | Blumenkranz ......... A61B 34/30 |
| | | 74/490.06 |
| 2011/0009863 A1 | 1/2011 | Stanislaw |
| 2011/0046441 A1 | 2/2011 | Wiltshire et al. |
| 2011/0077681 A1 | 3/2011 | Nagano |
| 2011/0090486 A1* | 4/2011 | Udd ....................... A61B 34/20 |
| | | 356/73.1 |
| 2011/0098533 A1 | 4/2011 | Onoda |
| 2011/0130718 A1 | 6/2011 | Kidd et al. |
| 2011/0148442 A1 | 6/2011 | Berner |
| 2011/0152880 A1 | 6/2011 | Alvarez et al. |
| 2011/0245844 A1 | 10/2011 | Jinno et al. |
| 2011/0261183 A1 | 10/2011 | Ma et al. |
| 2011/0306836 A1 | 12/2011 | Ohline et al. |
| 2012/0071894 A1 | 3/2012 | Tanner et al. |
| 2012/0071895 A1 | 3/2012 | Stahler et al. |
| 2012/0123327 A1 | 5/2012 | Miller |
| 2012/0136419 A1 | 5/2012 | Zarembo et al. |
| 2012/0143226 A1 | 6/2012 | Belson et al. |
| 2012/0190976 A1 | 7/2012 | Kleinstreuer |
| 2012/0191107 A1 | 7/2012 | Tanner et al. |
| 2012/0239012 A1 | 9/2012 | Laurent et al. |
| 2012/0259244 A1 | 10/2012 | Roberts et al. |
| 2012/0283747 A1 | 11/2012 | Popovic |
| 2012/0289777 A1 | 11/2012 | Chopra |
| 2013/0018400 A1 | 1/2013 | Milton et al. |
| 2013/0030519 A1 | 1/2013 | Tran et al. |
| 2013/0035537 A1 | 2/2013 | Wallace et al. |
| 2013/0090552 A1 | 4/2013 | Ramamurthy et al. |
| 2013/0109957 A1 | 5/2013 | Hooft et al. |
| 2013/0131499 A1* | 5/2013 | Chan ..................... A61B 8/0841 |
| | | 600/424 |
| 2013/0144116 A1 | 6/2013 | Cooper et al. |
| 2013/0165854 A1 | 6/2013 | Sandhu et al. |
| 2013/0165908 A1 | 6/2013 | Purdy et al. |
| 2013/0204124 A1 | 8/2013 | Duindam |
| 2013/0226151 A1 | 8/2013 | Suehara |
| 2013/0303892 A1 | 11/2013 | Zhao |
| 2013/0304091 A1 | 11/2013 | Straehnz |
| 2013/0317276 A1 | 11/2013 | D'Andrea |
| 2013/0317519 A1 | 11/2013 | Romo et al. |
| 2013/0345519 A1 | 12/2013 | Piskun et al. |
| 2014/0012288 A1 | 1/2014 | Darisse |
| 2014/0046313 A1 | 2/2014 | Pederson et al. |
| 2014/0053654 A1* | 2/2014 | Rogge .................... G01L 1/246 |
| | | 73/800 |
| 2014/0142591 A1 | 5/2014 | Alvarez et al. |
| 2014/0200402 A1 | 7/2014 | Snoke et al. |
| 2014/0235943 A1 | 8/2014 | Paris |
| 2014/0276594 A1 | 9/2014 | Tanner et al. |
| 2014/0316397 A1 | 10/2014 | Brown |
| 2014/0343416 A1 | 11/2014 | Panescu |
| 2014/0357984 A1 | 12/2014 | Wallace et al. |
| 2014/0364870 A1 | 12/2014 | Alvarez et al. |
| 2015/0031950 A1 | 1/2015 | Drontle et al. |
| 2015/0255782 A1 | 9/2015 | Kim et al. |
| 2016/0000414 A1 | 1/2016 | Brown |
| 2016/0001038 A1 | 1/2016 | Romo et al. |
| 2016/0007881 A1 | 1/2016 | Wong et al. |
| 2016/0067450 A1 | 3/2016 | Kowshik |
| 2016/0183841 A1 | 6/2016 | Duindam et al. |
| 2016/0227982 A1 | 8/2016 | Takahashi |
| 2016/0270865 A1 | 9/2016 | Landey et al. |
| 2016/0287279 A1 | 10/2016 | Bovay et al. |
| 2016/0287346 A1 | 10/2016 | Hyodo et al. |
| 2016/0346049 A1 | 12/2016 | Allen et al. |
| 2016/0372743 A1 | 12/2016 | Cho et al. |
| 2016/0374590 A1 | 12/2016 | Wong et al. |
| 2017/0007337 A1 | 1/2017 | Dan |
| 2017/0119481 A1 | 5/2017 | Romo et al. |
| 2017/0165011 A1 | 6/2017 | Bovay et al. |
| 2017/0202627 A1 | 7/2017 | Sramek et al. |

(56) References Cited

U.S. PATENT DOCUMENTS

| | | |
|---|---|---|
| 2017/0209073 A1 | 7/2017 | Sramek et al. |
| 2017/0281218 A1 | 10/2017 | Timm |
| 2017/0290631 A1 | 10/2017 | Lee et al. |
| 2017/0340396 A1 | 11/2017 | Romo et al. |
| 2017/0367782 A1 | 12/2017 | Schuh et al. |
| 2018/0025666 A1 | 1/2018 | Ho et al. |
| 2018/0214011 A1 | 8/2018 | Graetzel et al. |
| 2018/0221038 A1 | 8/2018 | Noonan et al. |
| 2018/0221039 A1 | 8/2018 | Shah |
| 2018/0235717 A1* | 8/2018 | Flexman ............ G02B 23/2469 |
| 2018/0250083 A1 | 9/2018 | Schuh et al. |
| 2018/0271616 A1 | 9/2018 | Schuh et al. |
| 2018/0279852 A1 | 10/2018 | Rafii-Tari et al. |
| 2018/0280660 A1 | 10/2018 | Landey et al. |
| 2018/0289431 A1 | 10/2018 | Draper et al. |
| 2018/0325499 A1 | 11/2018 | Landey et al. |
| 2018/0333044 A1 | 11/2018 | Jenkins |
| 2018/0360435 A1 | 12/2018 | Romo |
| 2019/0000559 A1 | 1/2019 | Berman et al. |
| 2019/0000560 A1 | 1/2019 | Berman et al. |
| 2019/0000576 A1 | 1/2019 | Mintz et al. |
| 2019/0083183 A1 | 3/2019 | Moll et al. |
| 2019/0110839 A1 | 4/2019 | Rafii-Tari et al. |
| 2019/0151148 A1 | 4/2019 | Alvarez et al. |
| 2019/0167366 A1 | 6/2019 | Ummalaneni |
| 2019/0175009 A1 | 6/2019 | Mintz |
| 2019/0175062 A1 | 6/2019 | Rafii-Tari et al. |
| 2019/0175799 A1 | 6/2019 | Hsu |
| 2019/0183585 A1 | 6/2019 | Rafii-Tari et al. |
| 2019/0183587 A1 | 6/2019 | Rafii-Tari et al. |
| 2019/0216548 A1 | 7/2019 | Ummalaneni |
| 2019/0216576 A1 | 7/2019 | Eyre |
| 2019/0223974 A1 | 7/2019 | Romo |
| 2019/0228525 A1 | 7/2019 | Mintz et al. |
| 2019/0246882 A1 | 8/2019 | Graetzel et al. |
| 2019/0262086 A1 | 8/2019 | Connolly et al. |
| 2019/0269468 A1 | 9/2019 | Hsu et al. |
| 2019/0274764 A1 | 9/2019 | Romo |
| 2019/0290109 A1 | 9/2019 | Agrawal et al. |
| 2019/0298160 A1 | 10/2019 | Ummalaneni et al. |
| 2019/0298460 A1 | 10/2019 | Al-Jadda |
| 2019/0298465 A1 | 10/2019 | Chin |
| 2019/0307987 A1 | 10/2019 | Yu |
| 2019/0328213 A1 | 10/2019 | Landey et al. |
| 2019/0336238 A1 | 11/2019 | Yu |
| 2019/0365209 A1 | 12/2019 | Ye et al. |
| 2019/0365479 A1 | 12/2019 | Rafii-Tari |
| 2019/0365486 A1 | 12/2019 | Srinivasan et al. |
| 2019/0374297 A1 | 12/2019 | Wallace et al. |
| 2019/0375383 A1 | 12/2019 | Alvarez |
| 2019/0380787 A1 | 12/2019 | Ye |
| 2019/0380797 A1 | 12/2019 | Yu |
| 2020/0000530 A1 | 1/2020 | DeFonzo |
| 2020/0000533 A1 | 1/2020 | Schuh |
| 2020/0022767 A1 | 1/2020 | Hill |
| 2020/0038128 A1 | 2/2020 | Joseph |
| 2020/0039086 A1 | 2/2020 | Meyer |
| 2020/0046434 A1 | 2/2020 | Graetzel |
| 2020/0046942 A1 | 2/2020 | Alvarez |
| 2020/0054405 A1 | 2/2020 | Schuh |
| 2020/0054408 A1 | 2/2020 | Schuh et al. |
| 2020/0060516 A1 | 2/2020 | Baez |
| 2020/0093549 A1 | 3/2020 | Chin |
| 2020/0093554 A1 | 3/2020 | Schuh |
| 2020/0100845 A1 | 4/2020 | Julian |
| 2020/0100855 A1 | 4/2020 | Leparmentier |
| 2020/0101264 A1 | 4/2020 | Jiang |
| 2020/0107894 A1 | 4/2020 | Wallace |
| 2020/0121502 A1 | 4/2020 | Kintz |
| 2020/0146769 A1 | 5/2020 | Eyre |
| 2020/0188043 A1 | 6/2020 | Yu |
| 2020/0197112 A1 | 6/2020 | Chin |
| 2020/0206472 A1 | 7/2020 | Ma |
| 2020/0217733 A1 | 7/2020 | Lin |
| 2020/0222134 A1 | 7/2020 | Schuh |
| 2020/0237458 A1 | 7/2020 | DeFonzo |
| 2020/0261172 A1 | 8/2020 | Romo |
| 2020/0268459 A1 | 8/2020 | Noonan et al. |
| 2020/0268460 A1 | 8/2020 | Tse |

FOREIGN PATENT DOCUMENTS

| | | |
|---|---|---|
| CN | 102316817 | 1/2012 |
| CN | 102458295 | 5/2012 |
| CN | 102665590 | 9/2012 |
| CN | 102711586 | 10/2012 |
| CN | 102973317 | 3/2013 |
| CN | 103767659 | 5/2014 |
| CN | 103930063 | 7/2014 |
| EP | 0 543 539 | 5/1993 |
| EP | 0 776 739 | 6/1997 |
| EP | 1 442 720 | 8/2004 |
| EP | 0 904 796 | 11/2004 |
| JP | 2006-525087 | 11/2006 |
| JP | 2007-511247 | 5/2007 |
| JP | 2010-046384 | 3/2010 |
| JP | 2011-015992 | 1/2011 |
| JP | 2012-105793 | 6/2012 |
| WO | WO 94/14494 | 7/1994 |
| WO | WO 00/67640 | 11/2000 |
| WO | WO 02/74178 | 9/2002 |
| WO | WO 04/039273 | 5/2004 |
| WO | WO 04/105849 | 12/2004 |
| WO | WO 05/032637 | 4/2005 |
| WO | WO 05/081202 | 9/2005 |
| WO | WO 09/097461 | 6/2007 |
| WO | WO 07/146987 | 12/2007 |
| WO | WO 08/097540 | 8/2008 |
| WO | WO 09/092059 | 7/2009 |
| WO | WO 10/081187 | 7/2010 |
| WO | WO 11/005335 | 1/2011 |
| WO | WO 13/107468 | 7/2013 |
| WO | WO 15/093602 | 12/2013 |
| WO | WO 16/003052 | 1/2016 |

* cited by examiner

SYSTEMS AND METHODS FOR OPTICAL STRAIN SENSING IN MEDICAL INSTRUMENTS

CROSS-REFERENCE TO RELATED APPLICATION(S)

This application claims the benefit of U.S. Provisional Application No. 62/826,825, filed Mar. 29, 2019, which is hereby incorporated by reference in its entirety.

TECHNICAL FIELD

The systems and methods disclosed herein are directed to medical instruments, and more particularly to sensing strain along medical instruments using optical fibers.

BACKGROUND

Robotic medical systems can include robotic arms configured to manipulate one or more medical instruments through a patient's anatomy. The manipulation of these medical instrument can be effected using one or more pull wires running along the length of the medical instruments. Certain medical instruments may also include one or more optical fibers running along the length thereof which may be used to sense the strain experienced by the medical instrument.

SUMMARY

The systems, methods and devices of this disclosure each have several innovative aspects, no single one of which is solely responsible for the desirable attributes disclosed herein.

In one aspect, there is provided a medical instrument, comprising: an elongated shaft; and at least one pull wire extending from a proximal end of the elongated shaft to the distal end of the elongated shaft, the at least pull wire configured to cause actuation of the medical instrument in at least one degree of freedom, wherein the at least one pull wire comprises an optical fiber configured to provide an indication of strain along the pull wire.

In another aspect, there is provided a medical robotic system, comprising: a medical instrument configured to be inserted into a region of a body, the medical instrument comprising: an elongated shaft, at least one pull wire extending from a proximal end of the elongated shaft to the distal end of the elongated shaft, the at least pull wire configured to cause actuation of the medical instrument in at least one degree of freedom, wherein the at least one pull wire comprises an optical fiber configured to provide an indication of strain along the pull wire; a sensor configured to generate strain data indicative of the strain at the position of at least one fiber Bragg grating (FBG) along the pull wire; and an instrument positioning device configured to be attached to the instrument and control movement of the instrument via actuation of the one or more pull wires.

In yet another aspect, there is provided a method of determining strain in a medical instrument, comprising: transmitting, from a sensor, light along at least one pull wire of the medical instrument, the medical instrument comprising: an elongated shaft, and the at least one pull wire extending from a proximal end of the elongated shaft to the distal end of the elongated shaft, the at least pull wire configured to cause actuation of the medical instrument in at least one degree of freedom; receiving, at the sensor, light reflected from the optical fiber of the pull wire; and generating, at the sensor, strain data indicative of strain along the pull wire based on the received light.

BRIEF DESCRIPTION OF THE DRAWINGS

The disclosed aspects will hereinafter be described in conjunction with the appended drawings, provided to illustrate and not to limit the disclosed aspects, wherein like designations denote like elements.

DETAILED DESCRIPTION

1. Overview.

Aspects of the present disclosure may be integrated into a robotically-enabled medical system capable of performing a variety of medical procedures, including both minimally invasive, such as laparoscopy, and non-invasive, such as endoscopy, procedures. Among endoscopy procedures, the system may be capable of performing bronchoscopy, ureteroscopy, gastroscopy, etc.

In addition to performing the breadth of procedures, the system may provide additional benefits, such as enhanced imaging and guidance to assist the physician. Additionally, the system may provide the physician with the ability to perform the procedure from an ergonomic position without the need for awkward arm motions and positions. Still further, the system may provide the physician with the ability to perform the procedure with improved ease of use such that one or more of the instruments of the system can be controlled by a single user.

Various embodiments will be described below in conjunction with the drawings for purposes of illustration. It should be appreciated that many other implementations of the disclosed concepts are possible, and various advantages can be achieved with the disclosed implementations. Headings are included herein for reference and to aid in locating various sections. These headings are not intended to limit the scope of the concepts described with respect thereto. Such concepts may have applicability throughout the entire specification.

A. Robotic System—Cart.

Figure 1:
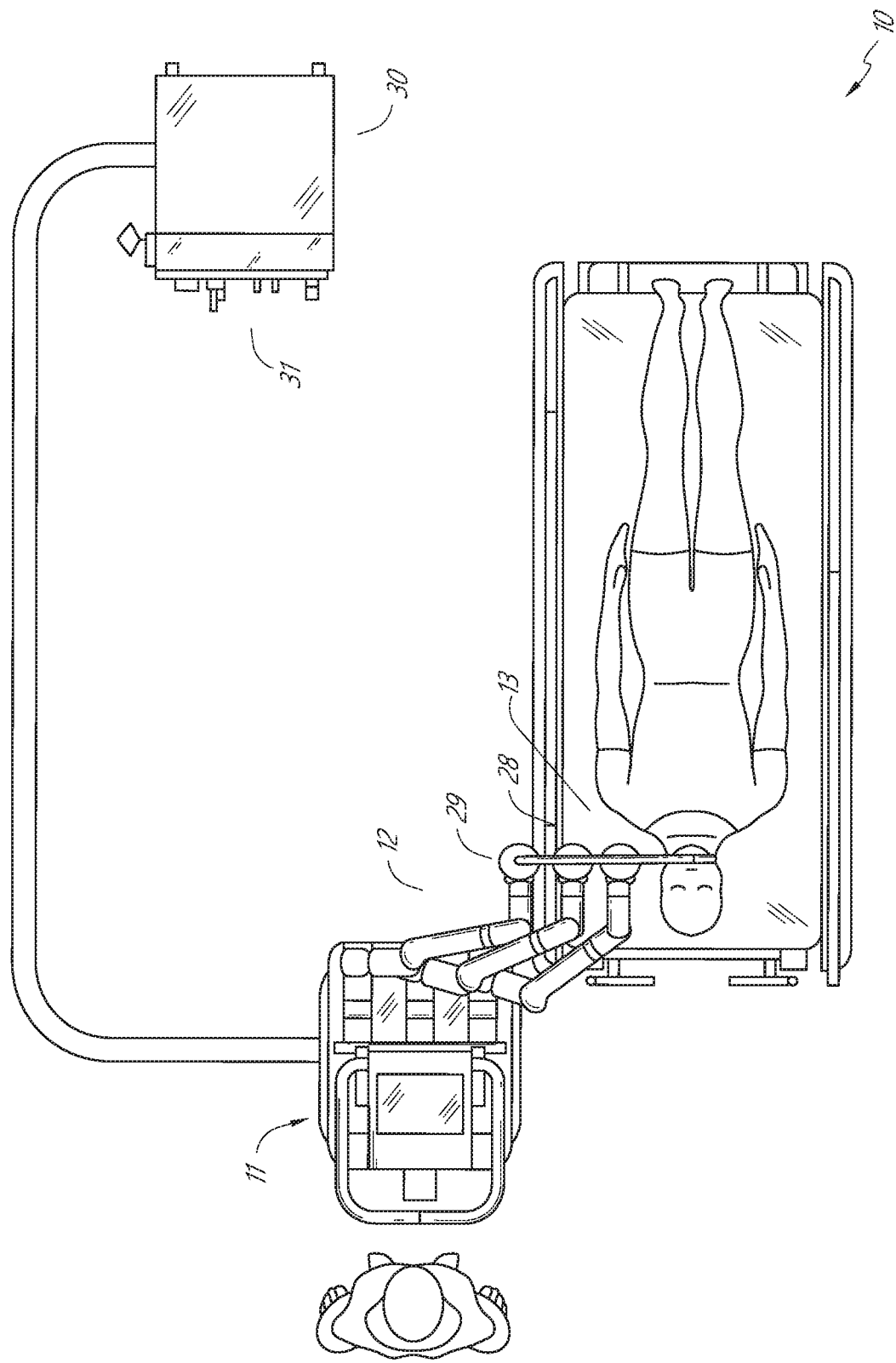
FIG. 1 illustrates an embodiment of a cart-based robotic system arranged for diagnostic and/or therapeutic bronchoscopy procedure(s).
Figure 2:
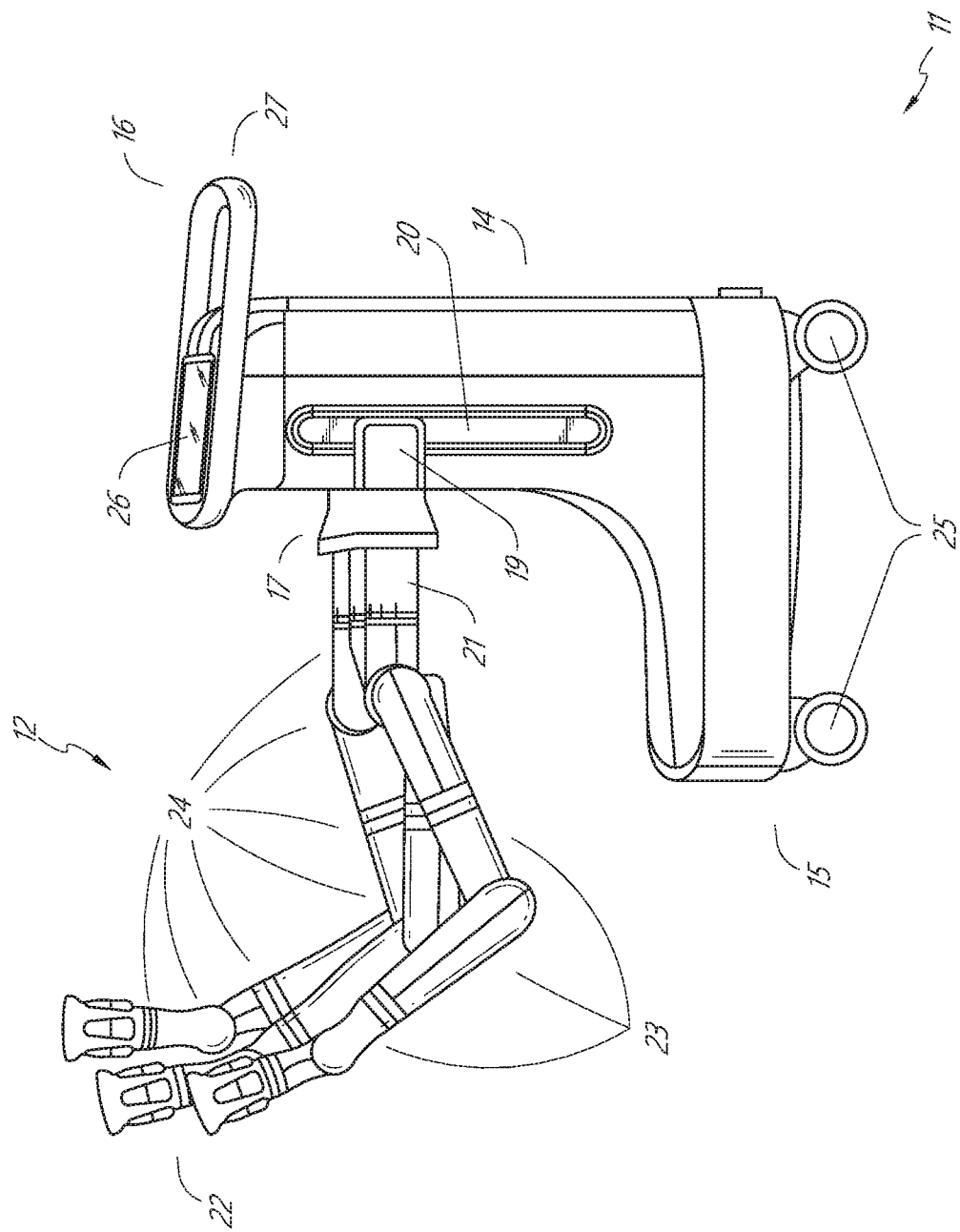
FIG. 2 depicts further aspects of the robotic system of FIG. 1.

The robotically-enabled medical system may be configured in a variety of ways depending on the particular procedure. FIG. 1 illustrates an embodiment of a cart-based robotically-enabled system 10 arranged for a diagnostic and/or therapeutic bronchoscopy procedure. During a bronchoscopy, the system 10 may comprise a cart 11 having one or more robotic arms 12 to deliver a medical instrument, such as a steerable endoscope 13, which may be a procedure-specific bronchoscope for bronchoscopy, to a natural orifice access point (i.e., the mouth of the patient positioned on a table in the present example) to deliver diagnostic and/or therapeutic tools. As shown, the cart 11 may be positioned proximate to the patient's upper torso in order to provide access to the access point. Similarly, the robotic arms 12 may be actuated to position the bronchoscope relative to the access point. The arrangement in FIG. 1 may also be utilized when performing a gastro-intestinal (GI) procedure with a gastroscope, a specialized endoscope for GI procedures. FIG. 2 depicts an example embodiment of the cart in greater detail.

With continued reference to FIG. 1, once the cart 11 is properly positioned, the robotic arms 12 may insert the steerable endoscope 13 into the patient robotically, manually, or a combination thereof. As shown, the steerable endoscope 13 may comprise at least two telescoping parts, such as an inner leader portion and an outer sheath portion, each portion coupled to a separate instrument driver from the set of instrument drivers 28, each instrument driver coupled to the distal end of an individual robotic arm. This linear arrangement of the instrument drivers 28, which facilitates coaxially aligning the leader portion with the sheath portion, creates a "virtual rail" 29 that may be repositioned in space by manipulating the one or more robotic arms 12 into different angles and/or positions. The virtual rails described herein are depicted in the Figures using dashed lines, and accordingly the dashed lines do not depict any physical structure of the system. Translation of the instrument drivers 28 along the virtual rail 29 telescopes the inner leader portion relative to the outer sheath portion or advances or retracts the endoscope 13 from the patient. The angle of the virtual rail 29 may be adjusted, translated, and pivoted based on clinical application or physician preference. For example, in bronchoscopy, the angle and position of the virtual rail 29 as shown represents a compromise between providing physician access to the endoscope 13 while minimizing friction that results from bending the endoscope 13 into the patient's mouth.

The endoscope 13 may be directed down the patient's trachea and lungs after insertion using precise commands from the robotic system until reaching the target destination or operative site. In order to enhance navigation through the patient's lung network and/or reach the desired target, the endoscope 13 may be manipulated to telescopically extend the inner leader portion from the outer sheath portion to obtain enhanced articulation and greater bend radius. The use of separate instrument drivers 28 also allows the leader portion and sheath portion to be driven independent of each other.

For example, the endoscope 13 may be directed to deliver a biopsy needle to a target, such as, for example, a lesion or nodule within the lungs of a patient. The needle may be deployed down a working channel that runs the length of the endoscope to obtain a tissue sample to be analyzed by a pathologist. Depending on the pathology results, additional tools may be deployed down the working channel of the endoscope for additional biopsies. After identifying a nodule to be malignant, the endoscope 13 may endoscopically deliver tools to resect the potentially cancerous tissue. In some instances, diagnostic and therapeutic treatments can be delivered in separate procedures. In those circumstances, the endoscope 13 may also be used to deliver a fiducial to "mark" the location of the target nodule as well. In other instances, diagnostic and therapeutic treatments may be delivered during the same procedure.

The system 10 may also include a movable tower 30, which may be connected via support cables to the cart 11 to provide support for controls, electronics, fluidics, optics, sensors, and/or power to the cart 11. Placing such functionality in the tower 30 allows for a smaller form factor cart 11 that may be more easily adjusted and/or repositioned by an operating physician and his/her staff. Additionally, the division of functionality between the cart/table and the support tower 30 reduces operating room clutter and facilitates improving clinical workflow. While the cart 11 may be positioned close to the patient, the tower 30 may be stowed in a remote location to stay out of the way during a procedure.

In support of the robotic systems described above, the tower 30 may include component(s) of a computer-based control system that stores computer program instructions, for example, within a non-transitory computer-readable storage medium such as a persistent magnetic storage drive, solid state drive, etc. The execution of those instructions, whether the execution occurs in the tower 30 or the cart 11, may control the entire system or sub-system(s) thereof. For example, when executed by a processor of the computer system, the instructions may cause the components of the robotics system to actuate the relevant carriages and arm mounts, actuate the robotics arms, and control the medical instruments. For example, in response to receiving the control signal, the motors in the joints of the robotics arms may position the arms into a certain posture.

The tower 30 may also include a pump, flow meter, valve control, and/or fluid access in order to provide controlled irrigation and aspiration capabilities to the system that may be deployed through the endoscope 13. These components may also be controlled using the computer system of tower 30. In some embodiments, irrigation and aspiration capabilities may be delivered directly to the endoscope 13 through separate cable(s).

The tower 30 may include a voltage and surge protector designed to provide filtered and protected electrical power to the cart 11, thereby avoiding placement of a power transformer and other auxiliary power components in the cart 11, resulting in a smaller, more moveable cart 11.

The tower 30 may also include support equipment for the sensors deployed throughout the robotic system 10. For example, the tower 30 may include opto-electronics equipment for detecting, receiving, and processing data received from the optical sensors or cameras throughout the robotic system 10. In combination with the control system, such opto-electronics equipment may be used to generate real-time images for display in any number of consoles deployed throughout the system, including in the tower 30. Similarly, the tower 30 may also include an electronic subsystem for receiving and processing signals received from deployed electromagnetic (EM) sensors. The tower 30 may also be used to house and position an EM field generator for detection by EM sensors in or on the medical instrument.

The tower 30 may also include a console 31 in addition to other consoles available in the rest of the system, e.g., console mounted on top of the cart. The console 31 may include a user interface and a display screen, such as a touchscreen, for the physician operator. Consoles in system 10 are generally designed to provide both robotic controls as well as pre-operative and real-time information of the procedure, such as navigational and localization information of the endoscope 13. When the console 31 is not the only console available to the physician, it may be used by a second operator, such as a nurse, to monitor the health or vitals of the patient and the operation of system, as well as provide procedure-specific data, such as navigational and localization information. In other embodiments, the console 30 is housed in a body that is separate from the tower 30.

The tower 30 may be coupled to the cart 11 and endoscope 13 through one or more cables or connections (not shown). In some embodiments, the support functionality from the tower 30 may be provided through a single cable to the cart 11, simplifying and de-cluttering the operating room. In other embodiments, specific functionality may be coupled in separate cabling and connections. For example, while power may be provided through a single power cable to the cart, the support for controls, optics, fluidics, and/or navigation may be provided through a separate cable.

FIG. 2 provides a detailed illustration of an embodiment of the cart from the cart-based robotically-enabled system shown in FIG. 1. The cart 11 generally includes an elongated support structure 14 (often referred to as a "column"), a cart base 15, and a console 16 at the top of the column 14. The column 14 may include one or more carriages, such as a carriage 17 (alternatively "arm support") for supporting the deployment of one or more robotic arms 12 (three shown in FIG. 2). The carriage 17 may include individually configurable arm mounts that rotate along a perpendicular axis to adjust the base of the robotic arms 12 for better positioning relative to the patient. The carriage 17 also includes a carriage interface 19 that allows the carriage 17 to vertically translate along the column 14.

The carriage interface 19 is connected to the column 14 through slots, such as slot 20, that are positioned on opposite sides of the column 14 to guide the vertical translation of the carriage 17. The slot 20 contains a vertical translation interface to position and hold the carriage at various vertical heights relative to the cart base 15. Vertical translation of the carriage 17 allows the cart 11 to adjust the reach of the robotic arms 12 to meet a variety of table heights, patient sizes, and physician preferences. Similarly, the individually configurable arm mounts on the carriage 17 allow the robotic arm base 21 of robotic arms 12 to be angled in a variety of configurations.

In some embodiments, the slot 20 may be supplemented with slot covers that are flush and parallel to the slot surface to prevent dirt and fluid ingress into the internal chambers of the column 14 and the vertical translation interface as the carriage 17 vertically translates. The slot covers may be deployed through pairs of spring spools positioned near the vertical top and bottom of the slot 20. The covers are coiled within the spools until deployed to extend and retract from their coiled state as the carriage 17 vertically translates up and down. The spring-loading of the spools provides force to retract the cover into a spool when carriage 17 translates towards the spool, while also maintaining a tight seal when the carriage 17 translates away from the spool. The covers may be connected to the carriage 17 using, for example, brackets in the carriage interface 19 to ensure proper extension and retraction of the cover as the carriage 17 translates.

The column 14 may internally comprise mechanisms, such as gears and motors, that are designed to use a vertically aligned lead screw to translate the carriage 17 in a mechanized fashion in response to control signals generated in response to user inputs, e.g., inputs from the console 16.

The robotic arms 12 may generally comprise robotic arm bases 21 and end effectors 22, separated by a series of linkages 23 that are connected by a series of joints 24, each joint comprising an independent actuator, each actuator comprising an independently controllable motor. Each independently controllable joint represents an independent degree of freedom available to the robotic arm. Each of the arms 12 have seven joints, and thus provide seven degrees of freedom. A multitude of joints result in a multitude of degrees of freedom, allowing for "redundant" degrees of freedom. Redundant degrees of freedom allow the robotic arms 12 to position their respective end effectors 22 at a specific position, orientation, and trajectory in space using different linkage positions and joint angles. This allows for the system to position and direct a medical instrument from a desired point in space while allowing the physician to move the arm joints into a clinically advantageous position away from the patient to create greater access, while avoiding arm collisions.

The cart base 15 balances the weight of the column 14, carriage 17, and arms 12 over the floor. Accordingly, the cart base 15 houses heavier components, such as electronics, motors, power supply, as well as components that either enable movement and/or immobilize the cart. For example, the cart base 15 includes rollable wheel-shaped casters 25 that allow for the cart to easily move around the room prior to a procedure. After reaching the appropriate position, the casters 25 may be immobilized using wheel locks to hold the cart 11 in place during the procedure.

Positioned at the vertical end of column 14, the console 16 allows for both a user interface for receiving user input and a display screen (or a dual-purpose device such as, for example, a touchscreen 26) to provide the physician user with both pre-operative and intra-operative data. Potential pre-operative data on the touchscreen 26 may include pre-operative plans, navigation and mapping data derived from pre-operative computerized tomography (CT) scans, and/or notes from pre-operative patient interviews. Intra-operative data on display may include optical information provided from the tool, sensor and coordinate information from sensors, as well as vital patient statistics, such as respiration, heart rate, and/or pulse. The console 16 may be positioned and tilted to allow a physician to access the console from the side of the column 14 opposite carriage 17. From this position, the physician may view the console 16, robotic arms 12, and patient while operating the console 16 from behind the cart 11. As shown, the console 16 also includes a handle 27 to assist with maneuvering and stabilizing cart 11.

Figure 3:
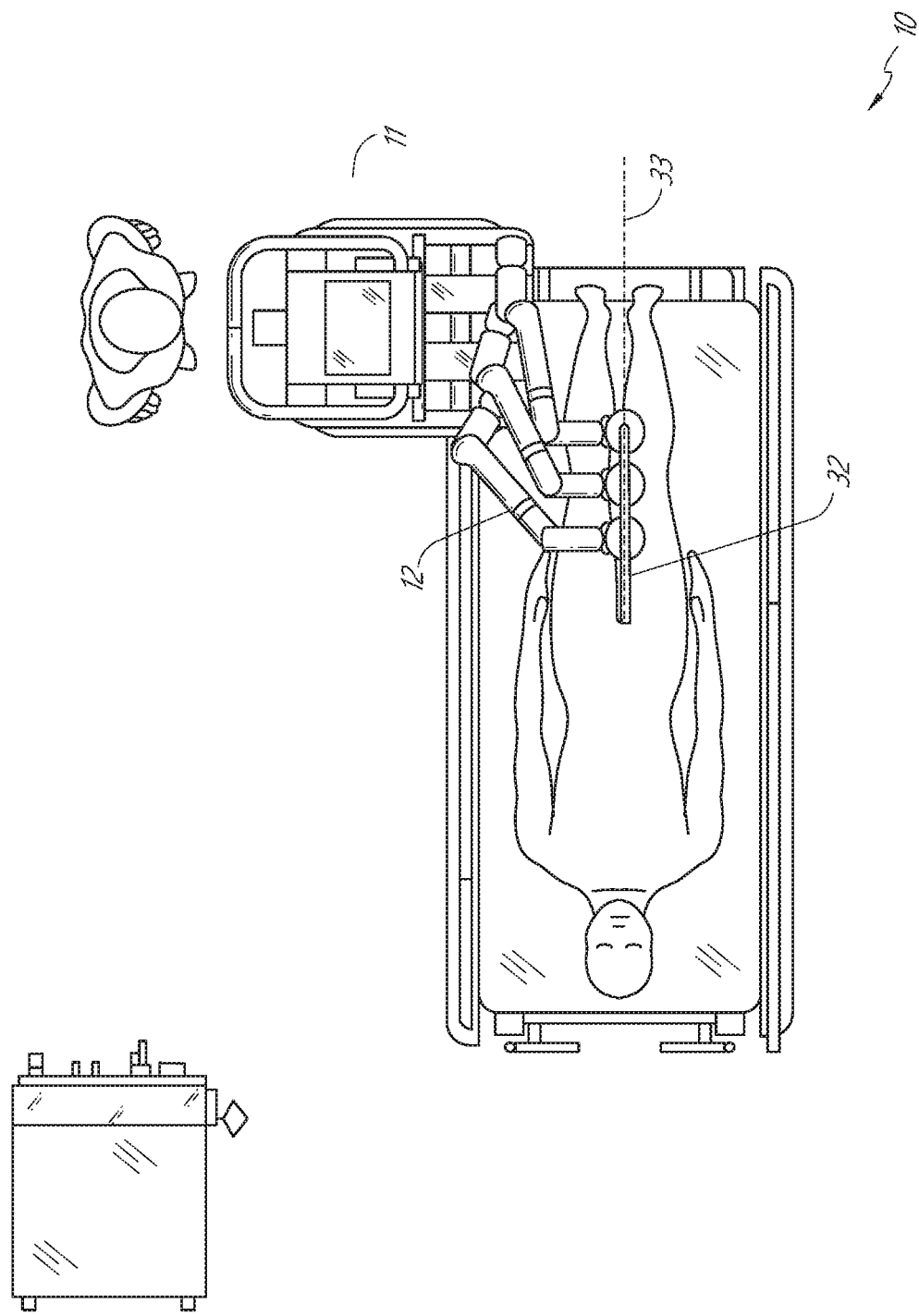
FIG. 3 illustrates an embodiment of the robotic system of FIG. 1 arranged for ureteroscopy.

FIG. 3 illustrates an embodiment of a robotically-enabled system 10 arranged for ureteroscopy. In a ureteroscopic procedure, the cart 11 may be positioned to deliver a ureteroscope 32, a procedure-specific endoscope designed to traverse a patient's urethra and ureter, to the lower abdominal area of the patient. In a ureteroscopy, it may be desirable for the ureteroscope 32 to be directly aligned with the patient's urethra to reduce friction and forces on the sensitive anatomy in the area. As shown, the cart 11 may be aligned at the foot of the table to allow the robotic arms 12 to position the ureteroscope 32 for direct linear access to the patient's urethra. From the foot of the table, the robotic arms 12 may insert the ureteroscope 32 along the virtual rail 33 directly into the patient's lower abdomen through the urethra.

After insertion into the urethra, using similar control techniques as in bronchoscopy, the ureteroscope 32 may be navigated into the bladder, ureters, and/or kidneys for diagnostic and/or therapeutic applications. For example, the ureteroscope 32 may be directed into the ureter and kidneys to break up kidney stone build up using a laser or ultrasonic lithotripsy device deployed down the working channel of the ureteroscope 32. After lithotripsy is complete, the resulting stone fragments may be removed using baskets deployed down the ureteroscope 32.

Figure 4:
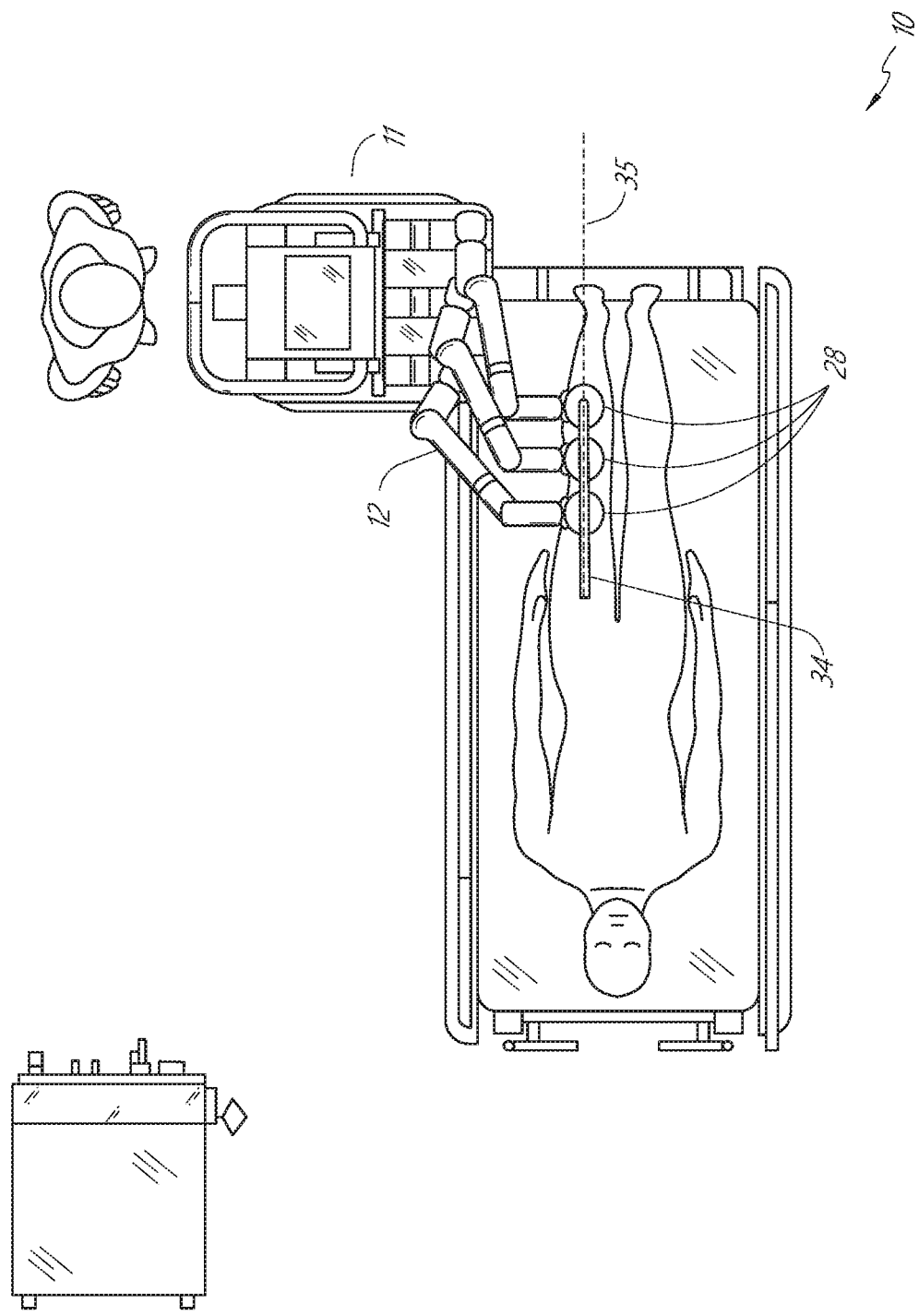
FIG. 4 illustrates an embodiment of the robotic system of FIG. 1 arranged for a vascular procedure.

FIG. 4 illustrates an embodiment of a robotically-enabled system similarly arranged for a vascular procedure. In a vascular procedure, the system 10 may be configured such that the cart 11 may deliver a medical instrument 34, such as a steerable catheter, to an access point in the femoral artery in the patient's leg. The femoral artery presents both a larger diameter for navigation as well as a relatively less circuitous and tortuous path to the patient's heart, which simplifies navigation. As in a ureteroscopic procedure, the cart 11 may be positioned towards the patient's legs and lower abdomen to allow the robotic arms 12 to provide a virtual rail 35 with direct linear access to the femoral artery access point in the patient's thigh/hip region. After insertion into the artery, the medical instrument 34 may be directed and inserted by translating the instrument drivers 28. Alternatively, the cart may be positioned around the patient's upper abdomen in order to reach alternative vascular access points, such as, for example, the carotid and brachial arteries near the shoulder and wrist.

B. Robotic System—Table.

Figure 5:
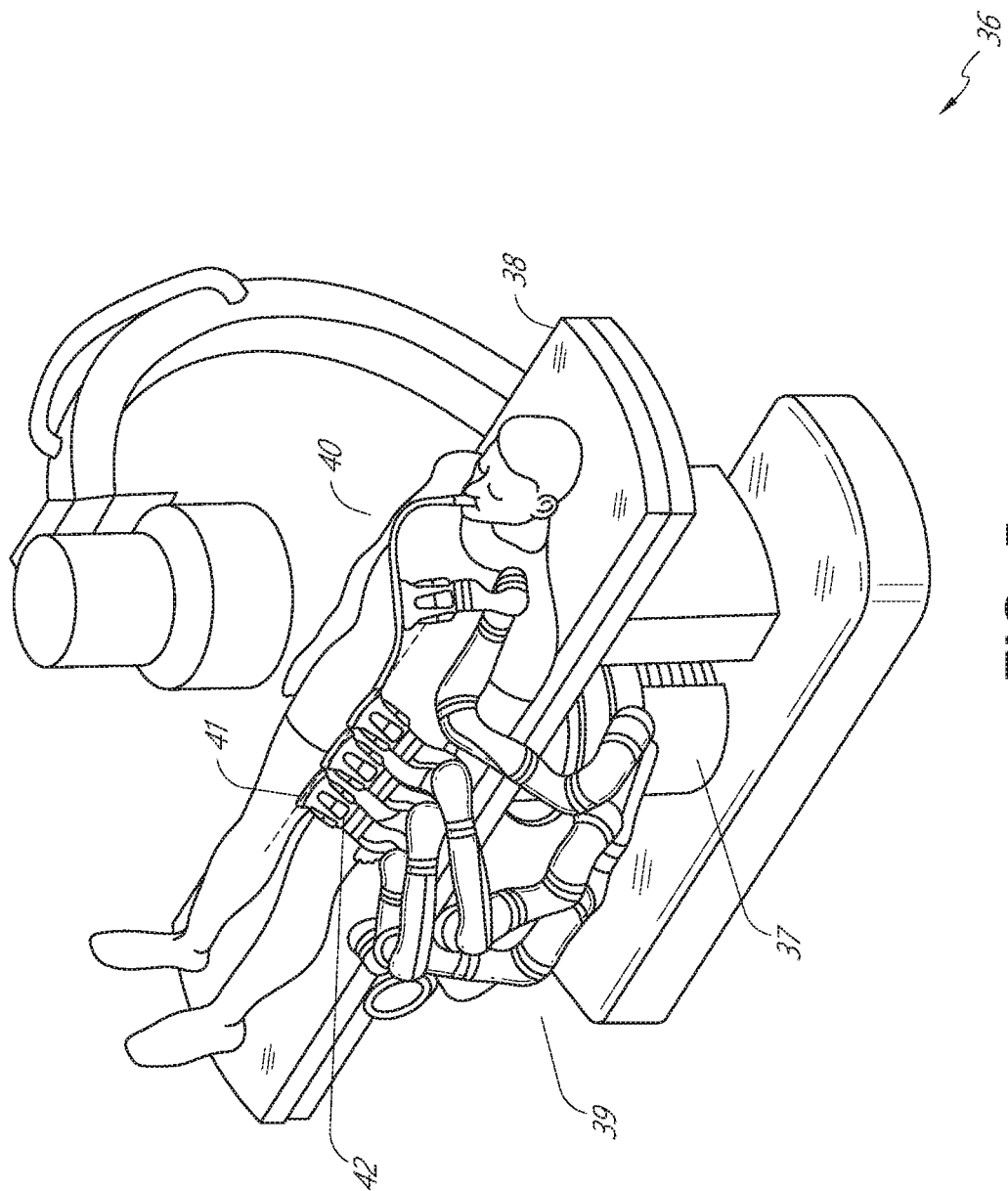
FIG. 5 illustrates an embodiment of a table-based robotic system arranged for a bronchoscopy procedure.

Embodiments of the robotically-enabled medical system may also incorporate the patient's table. Incorporation of the table reduces the amount of capital equipment within the operating room by removing the cart, which allows greater access to the patient. FIG. 5 illustrates an embodiment of such a robotically-enabled system arranged for a bronchoscopy procedure. System 36 includes a support structure or column 37 for supporting platform 38 (shown as a "table" or "bed") over the floor. Much like in the cart-based systems, the end effectors of the robotic arms 39 of the system 36 comprise instrument drivers 42 that are designed to manipulate an elongated medical instrument, such as a bronchoscope 40 in FIG. 5, through or along a virtual rail 41 formed from the linear alignment of the instrument drivers 42. In practice, a C-arm for providing fluoroscopic imaging may be positioned over the patient's upper abdominal area by placing the emitter and detector around table 38.

Figure 6:
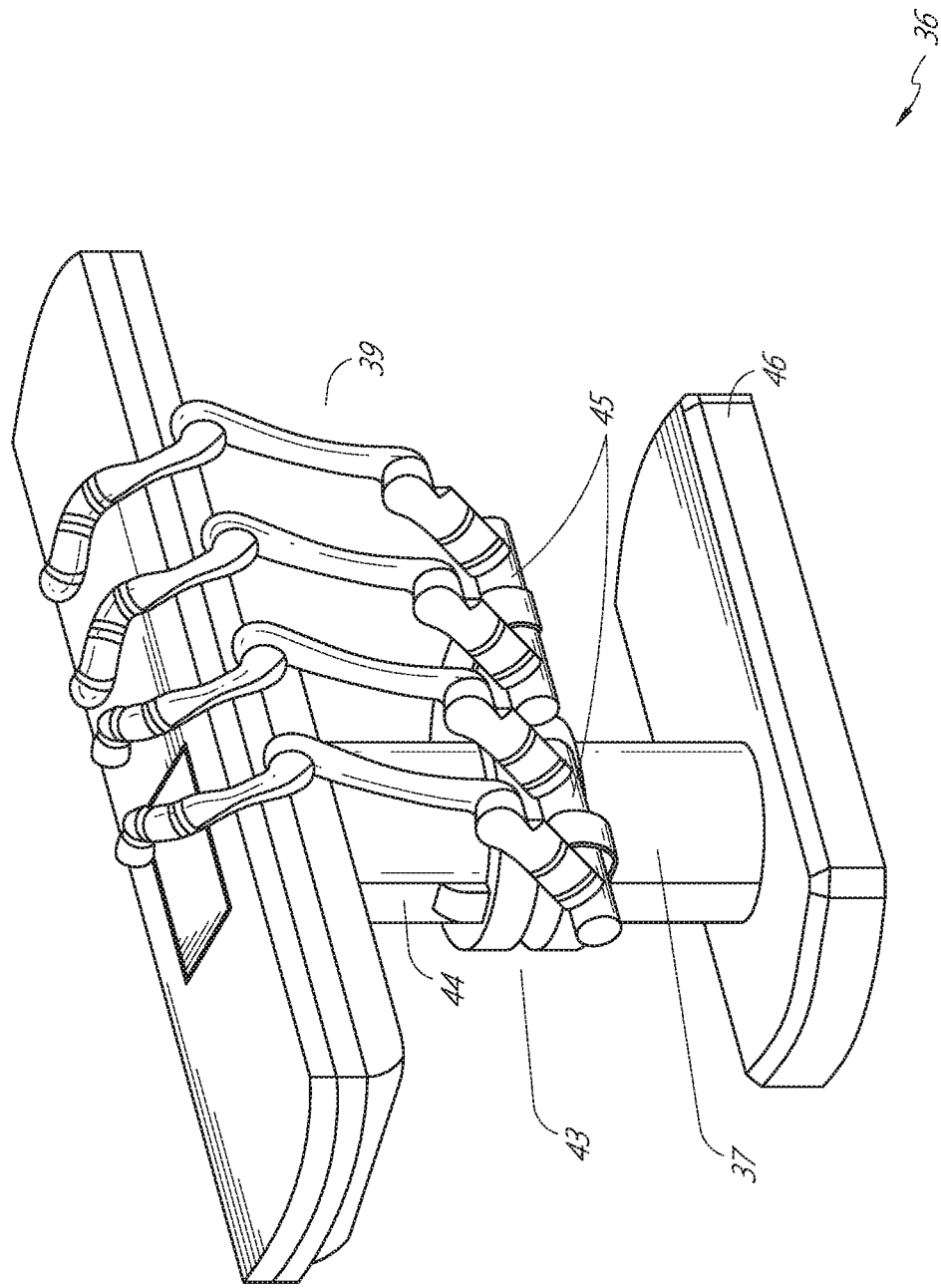
FIG. 6 provides an alternative view of the robotic system of FIG. 5.

FIG. 6 provides an alternative view of the system 36 without the patient and medical instrument for discussion purposes. As shown, the column 37 may include one or more carriages 43 shown as ring-shaped in the system 36, from which the one or more robotic arms 39 may be based. The carriages 43 may translate along a vertical column interface 44 that runs the length of the column 37 to provide different vantage points from which the robotic arms 39 may be positioned to reach the patient. The carriage(s) 43 may rotate around the column 37 using a mechanical motor positioned within the column 37 to allow the robotic arms 39 to have access to multiples sides of the table 38, such as, for example, both sides of the patient. In embodiments with multiple carriages, the carriages may be individually positioned on the column and may translate and/or rotate independent of the other carriages. While carriages 43 need not surround the column 37 or even be circular, the ring-shape as shown facilitates rotation of the carriages 43 around the column 37 while maintaining structural balance. Rotation and translation of the carriages 43 allows the system to align the medical instruments, such as endoscopes and laparoscopes, into different access points on the patient. In other embodiments (not shown), the system 36 can include a patient table or bed with adjustable arm supports in the form of bars or rails extending alongside it. One or more robotic arms 39 (e.g., via a shoulder with an elbow joint) can be attached to the adjustable arm supports, which can be vertically adjusted. By providing vertical adjustment, the robotic arms 39 are advantageously capable of being stowed compactly beneath the patient table or bed, and subsequently raised during a procedure.

Figure 9:
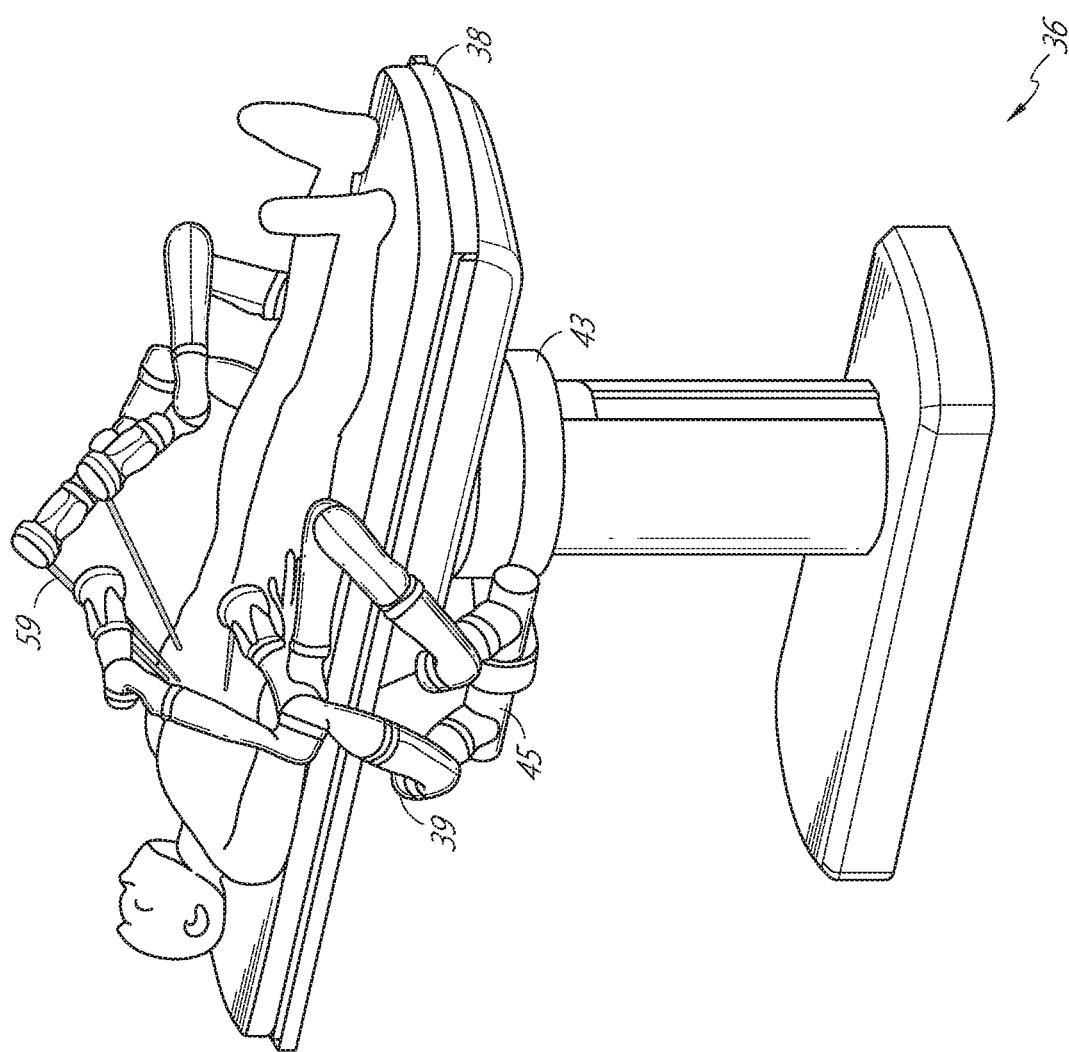
FIG. 9 illustrates an embodiment of a table-based robotic system configured for a laparoscopic procedure.

The arms 39 may be mounted on the carriages through a set of arm mounts 45 comprising a series of joints that may individually rotate and/or telescopically extend to provide additional configurability to the robotic arms 39. Additionally, the arm mounts 45 may be positioned on the carriages 43 such that, when the carriages 43 are appropriately rotated, the arm mounts 45 may be positioned on either the same side of table 38 (as shown in FIG. 6), on opposite sides of table 38 (as shown in FIG. 9), or on adjacent sides of the table 38 (not shown).

The column 37 structurally provides support for the table 38, and a path for vertical translation of the carriages. Internally, the column 37 may be equipped with lead screws for guiding vertical translation of the carriages, and motors to mechanize the translation of said carriages based the lead screws. The column 37 may also convey power and control signals to the carriage 43 and robotic arms 39 mounted thereon.

The table base 46 serves a similar function as the cart base 15 in cart 11 shown in FIG. 2, housing heavier components to balance the table/bed 38, the column 37, the carriages 43, and the robotic arms 39. The table base 46 may also incorporate rigid casters to provide stability during procedures. Deployed from the bottom of the table base 46, the casters may extend in opposite directions on both sides of the base 46 and retract when the system 36 needs to be moved.

Continuing with FIG. 6, the system 36 may also include a tower (not shown) that divides the functionality of system 36 between table and tower to reduce the form factor and bulk of the table. As in earlier disclosed embodiments, the tower may provide a variety of support functionalities to table, such as processing, computing, and control capabilities, power, fluidics, and/or optical and sensor processing. The tower may also be movable to be positioned away from the patient to improve physician access and de-clutter the operating room. Additionally, placing components in the tower allows for more storage space in the table base for potential stowage of the robotic arms. The tower may also include a master controller or console that provides both a user interface for user input, such as keyboard and/or pendant, as well as a display screen (or touchscreen) for pre-operative and intra-operative information, such as real-time imaging, navigation, and tracking information. In some embodiments, the tower may also contain holders for gas tanks to be used for insufflation.

Figure 7:
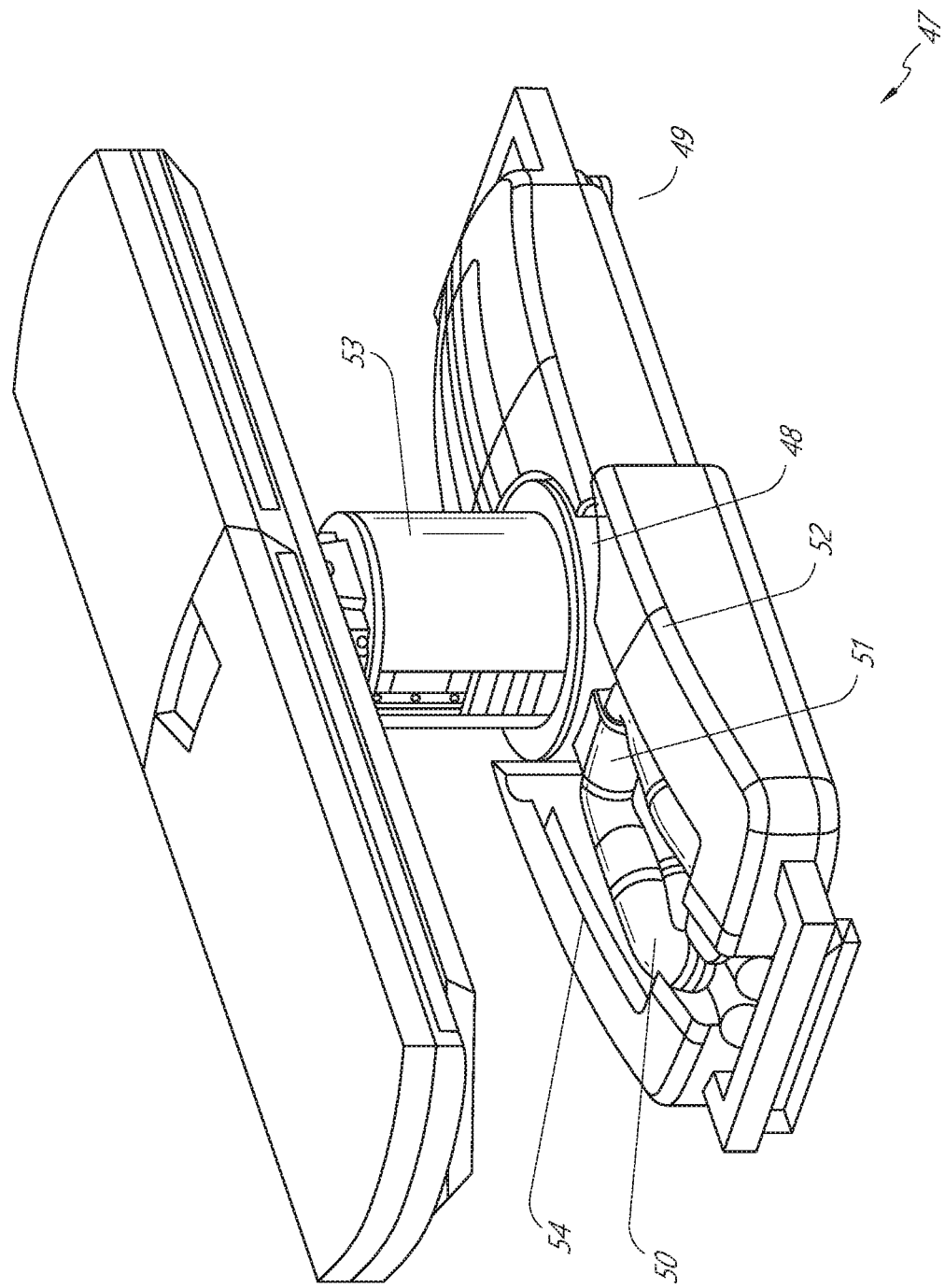
FIG. 7 illustrates an example system configured to stow robotic arm(s).

In some embodiments, a table base may stow and store the robotic arms when not in use. FIG. 7 illustrates a system 47 that stows robotic arms in an embodiment of the table-based system. In system 47, carriages 48 may be vertically translated into base 49 to stow robotic arms 50, arm mounts 51, and the carriages 48 within the base 49. Base covers 52 may be translated and retracted open to deploy the carriages 48, arm mounts 51, and arms 50 around column 53, and closed to stow to protect them when not in use. The base covers 52 may be sealed with a membrane 54 along the edges of its opening to prevent dirt and fluid ingress when closed.

Figure 8:
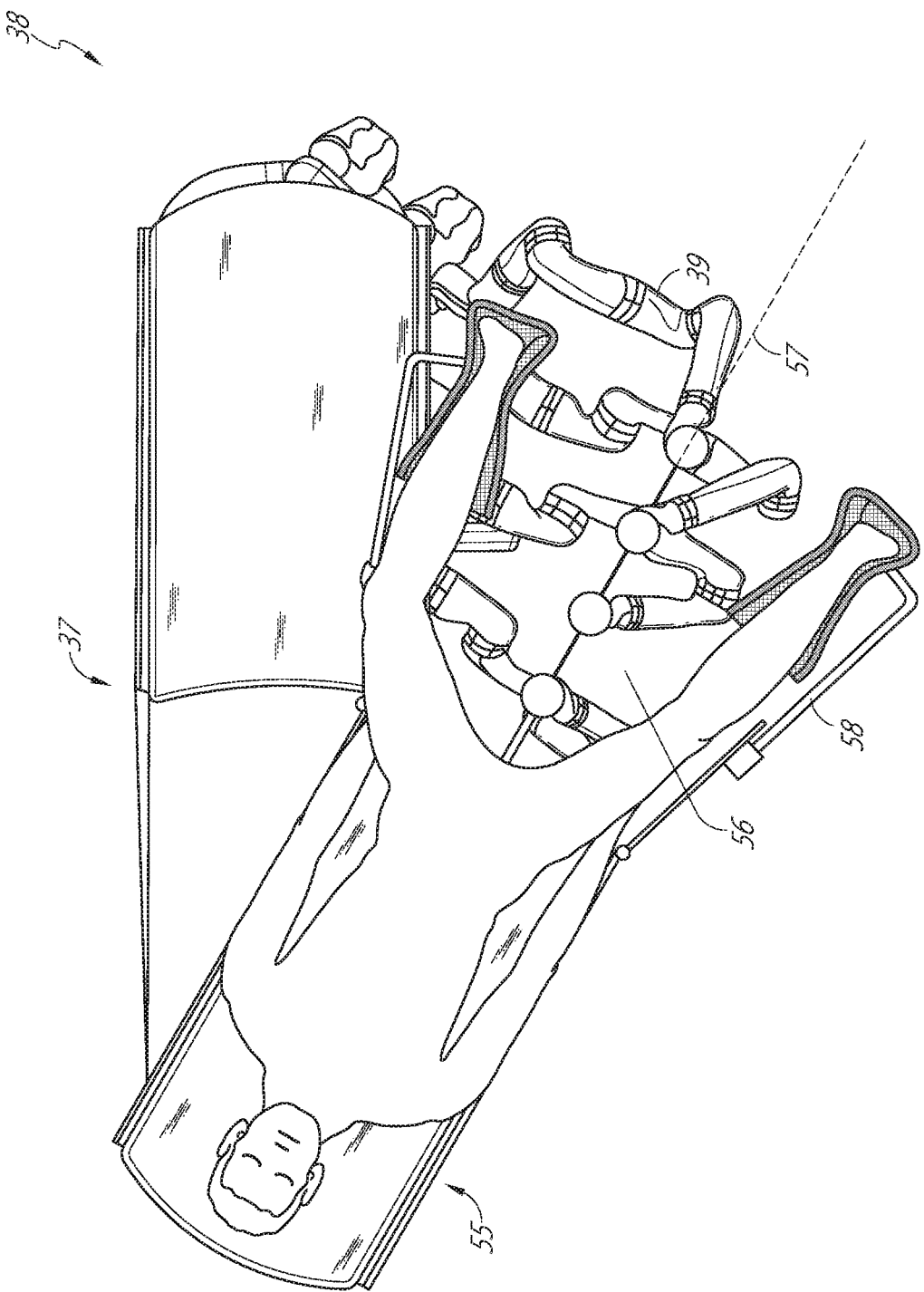
FIG. 8 illustrates an embodiment of a table-based robotic system configured for a ureteroscopy procedure.

FIG. 8 illustrates an embodiment of a robotically-enabled table-based system configured for a ureteroscopy procedure. In a ureteroscopy, the table 38 may include a swivel portion 55 for positioning a patient off-angle from the column 37 and table base 46. The swivel portion 55 may rotate or pivot around a pivot point (e.g., located below the patient's head) in order to position the bottom portion of the swivel portion 55 away from the column 37. For example, the pivoting of the swivel portion 55 allows a C-arm (not shown) to be positioned over the patient's lower abdomen without competing for space with the column (not shown) below table 38. By rotating the carriage 35 (not shown) around the column 37, the robotic arms 39 may directly insert a ureteroscope 56 along a virtual rail 57 into the patient's groin area to reach the urethra. In a ureteroscopy, stirrups 58 may also be fixed to the swivel portion 55 of the table 38 to support the position of the patient's legs during the procedure and allow clear access to the patient's groin area.

In a laparoscopic procedure, through small incision(s) in the patient's abdominal wall, minimally invasive instruments may be inserted into the patient's anatomy. In some embodiments, the minimally invasive instruments comprise an elongated rigid member, such as a shaft, which is used to access anatomy within the patient. After inflation of the patient's abdominal cavity, the instruments may be directed to perform surgical or medical tasks, such as grasping, cutting, ablating, suturing, etc. In some embodiments, the instruments can comprise a scope, such as a laparoscope. FIG. 9 illustrates an embodiment of a robotically-enabled table-based system configured for a laparoscopic procedure. As shown in FIG. 9, the carriages 43 of the system 36 may be rotated and vertically adjusted to position pairs of the robotic arms 39 on opposite sides of the table 38, such that instrument 59 may be positioned using the arm mounts 45 to be passed through minimal incisions on both sides of the patient to reach his/her abdominal cavity.

Figure 10:
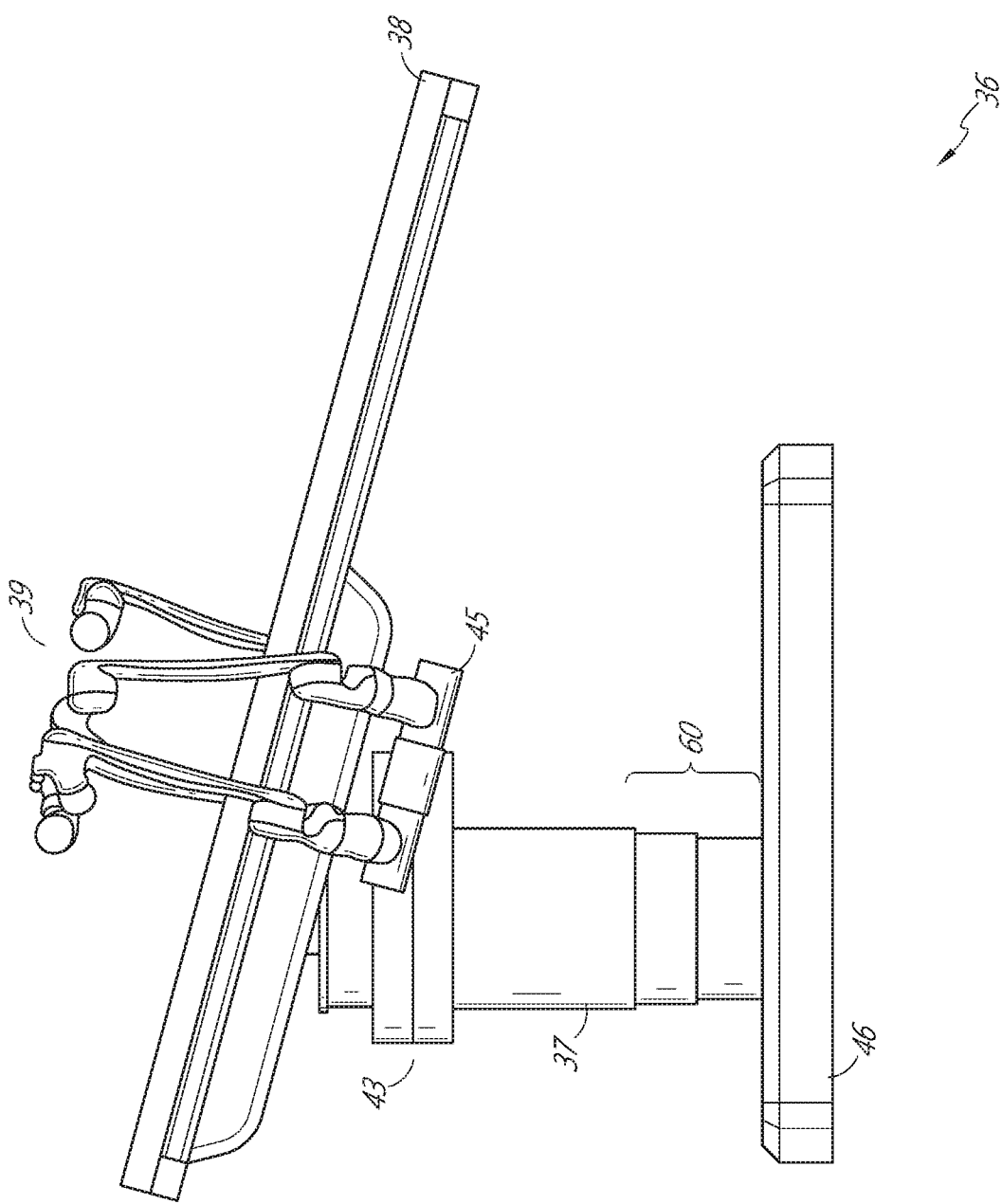
FIG. 10 illustrates an embodiment of the table-based robotic system of FIGS. 5-9 with pitch or tilt adjustment.

To accommodate laparoscopic procedures, the robotically-enabled table system may also tilt the platform to a desired angle. FIG. 10 illustrates an embodiment of the robotically-enabled medical system with pitch or tilt adjustment. As shown in FIG. 10, the system 36 may accommodate tilt of the table 38 to position one portion of the table at a greater distance from the floor than the other. Additionally, the arm mounts 45 may rotate to match the tilt such that the arms 39 maintain the same planar relationship with table 38. To accommodate steeper angles, the column 37 may also include telescoping portions 60 that allow vertical extension of column 37 to keep the table 38 from touching the floor or colliding with base 46.

Figure 11:
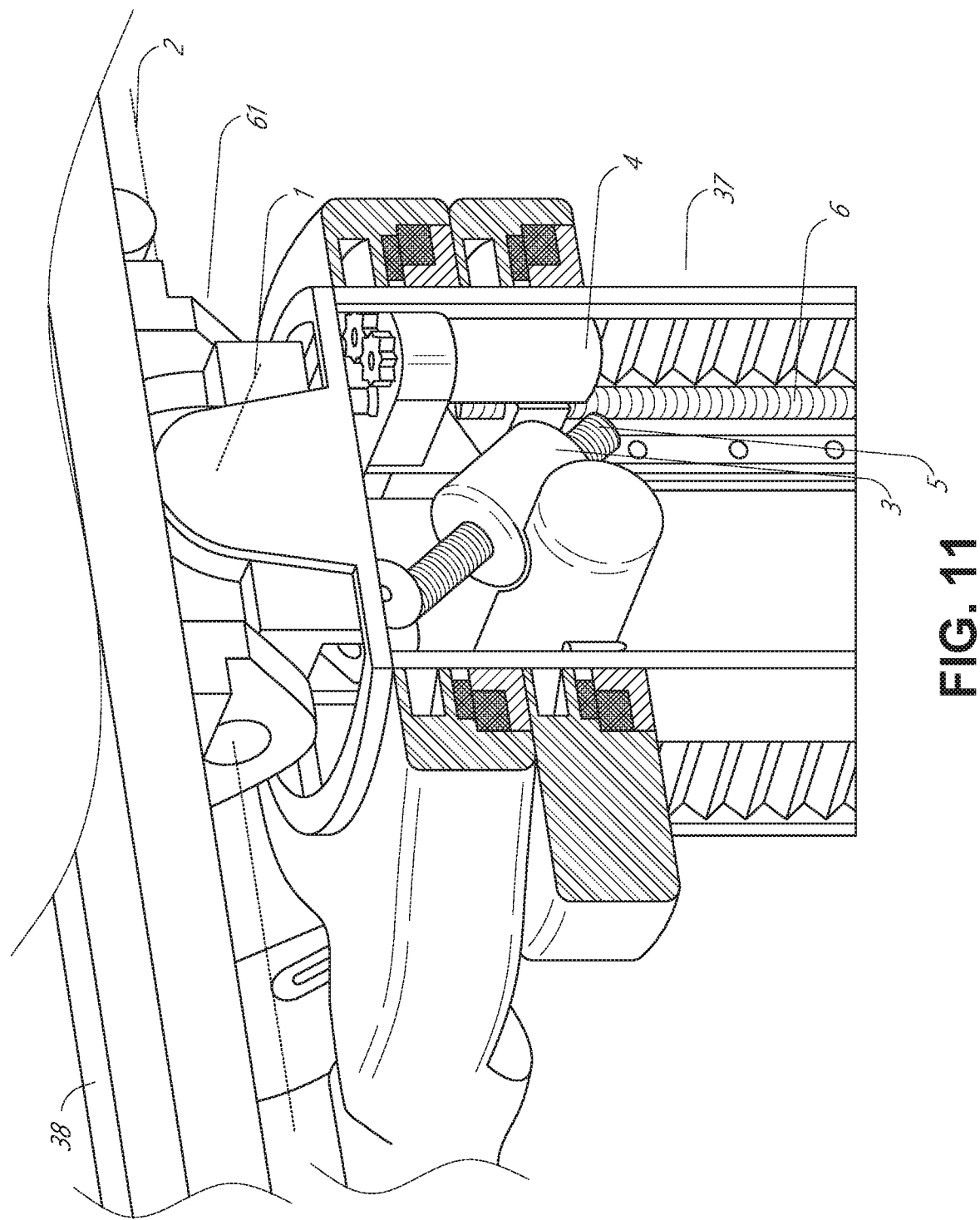
FIG. 11 provides a detailed illustration of the interface between the table and the column of the table-based robotic system of FIGS. 5-10.

FIG. 11 provides a detailed illustration of the interface between the table 38 and the column 37. Pitch rotation mechanism 61 may be configured to alter the pitch angle of the table 38 relative to the column 37 in multiple degrees of freedom. The pitch rotation mechanism 61 may be enabled by the positioning of orthogonal axes 1, 2 at the column-table interface, each axis actuated by a separate motor 3, 4 responsive to an electrical pitch angle command. Rotation along one screw 5 would enable tilt adjustments in one axis 1, while rotation along the other screw 6 would enable tilt adjustments along the other axis 2. In some embodiments, a ball joint can be used to alter the pitch angle of the table 38 relative to the column 37 in multiple degrees of freedom.

For example, pitch adjustments are particularly useful when trying to position the table in a Trendelenburg position, i.e., position the patient's lower abdomen at a higher position from the floor than the patient's lower abdomen, for lower abdominal surgery. The Trendelenburg position causes the patient's internal organs to slide towards his/her upper abdomen through the force of gravity, clearing out the abdominal cavity for minimally invasive tools to enter and perform lower abdominal surgical or medical procedures, such as laparoscopic prostatectomy.

Figure 12:
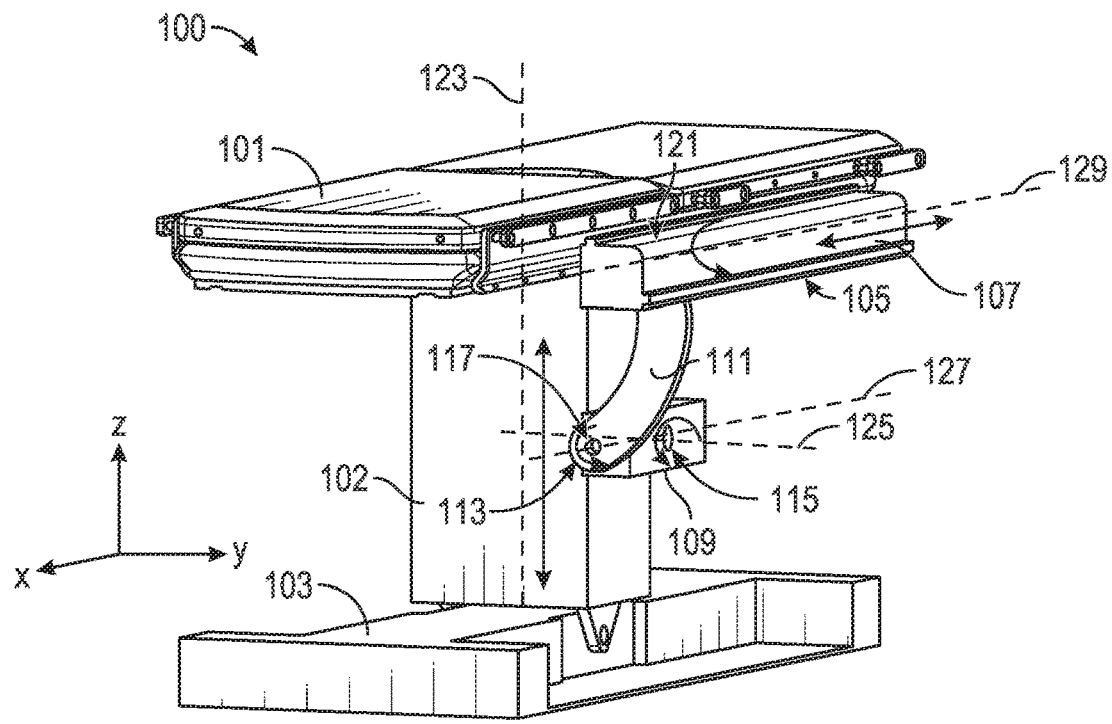
FIG. 12 illustrates an alternative embodiment of a table-based robotic system.
Figure 13:
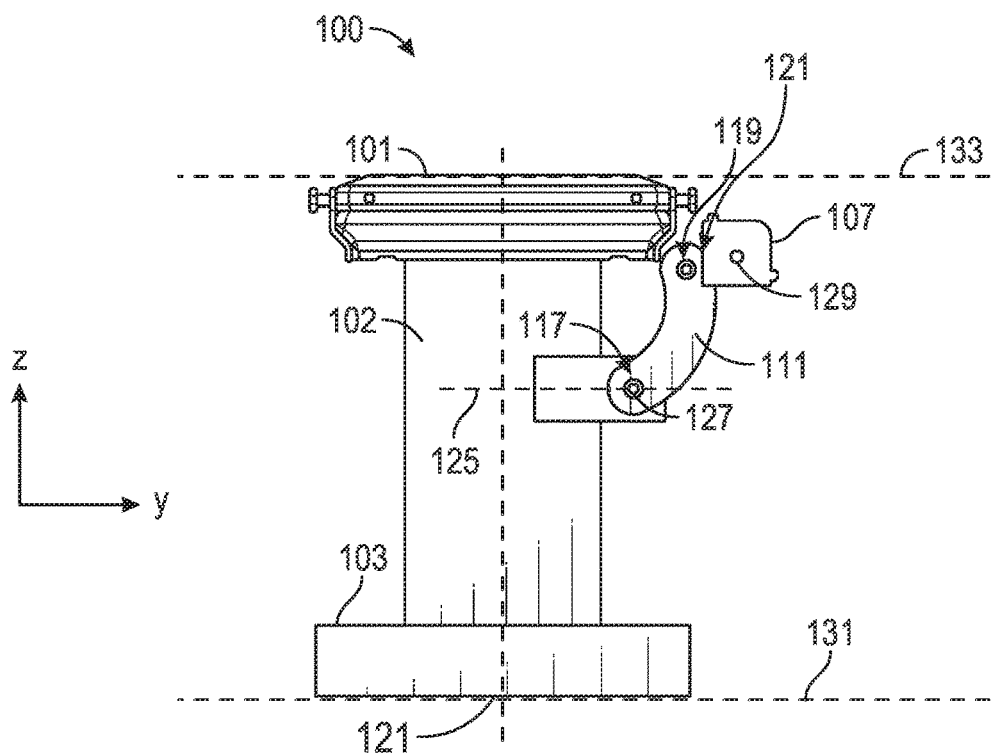
FIG. 13 illustrates an end view of the table-based robotic system of FIG. 12.

FIGS. 12 and 13 illustrate isometric and end views of an alternative embodiment of a table-based surgical robotics system 100. The surgical robotics system 100 includes one or more adjustable arm supports 105 that can be configured to support one or more robotic arms (see, for example, FIG. 14) relative to a table 101. In the illustrated embodiment, a single adjustable arm support 105 is shown, though an additional arm support can be provided on an opposite side of the table 101. The adjustable arm support 105 can be configured so that it can move relative to the table 101 to adjust and/or vary the position of the adjustable arm support 105 and/or any robotic arms mounted thereto relative to the table 101. For example, the adjustable arm support 105 may be adjusted one or more degrees of freedom relative to the table 101. The adjustable arm support 105 provides high versatility to the system 100, including the ability to easily stow the one or more adjustable arm supports 105 and any robotics arms attached thereto beneath the table 101. The adjustable arm support 105 can be elevated from the stowed position to a position below an upper surface of the table 101. In other embodiments, the adjustable arm support 105 can be elevated from the stowed position to a position above an upper surface of the table 101.

The adjustable arm support 105 can provide several degrees of freedom, including lift, lateral translation, tilt, etc. In the illustrated embodiment of FIGS. 12 and 13, the arm support 105 is configured with four degrees of freedom, which are illustrated with arrows in FIG. 12. A first degree of freedom allows for adjustment of the adjustable arm support 105 in the z-direction ("Z-lift"). For example, the adjustable arm support 105 can include a carriage 109 configured to move up or down along or relative to a column 102 supporting the table 101. A second degree of freedom can allow the adjustable arm support 105 to tilt. For example, the adjustable arm support 105 can include a rotary joint, which can allow the adjustable arm support 105 to be aligned with the bed in a Trendelenburg position. A third degree of freedom can allow the adjustable arm support 105 to "pivot up," which can be used to adjust a distance between a side of the table 101 and the adjustable arm support 105. A fourth degree of freedom can permit translation of the adjustable arm support 105 along a longitudinal length of the table.

The surgical robotics system 100 in FIGS. 12 and 13 can comprise a table supported by a column 102 that is mounted to a base 103. The base 103 and the column 102 support the table 101 relative to a support surface. A floor axis 131 and a support axis 133 are shown in FIG. 13.

The adjustable arm support 105 can be mounted to the column 102. In other embodiments, the arm support 105 can be mounted to the table 101 or base 103. The adjustable arm support 105 can include a carriage 109, a bar or rail connector 111 and a bar or rail 107. In some embodiments, one or more robotic arms mounted to the rail 107 can translate and move relative to one another.

The carriage 109 can be attached to the column 102 by a first joint 113, which allows the carriage 109 to move relative to the column 102 (e.g., such as up and down a first or vertical axis 123). The first joint 113 can provide the first degree of freedom (Z-lift) to the adjustable arm support 105. The adjustable arm support 105 can include a second joint 115, which provides the second degree of freedom (tilt) for the adjustable arm support 105. The adjustable arm support 105 can include a third joint 117, which can provide the third degree of freedom ("pivot up") for the adjustable arm support 105. An additional joint 119 (shown in FIG. 13) can be provided that mechanically constrains the third joint 117 to maintain an orientation of the rail 107 as the rail connector 111 is rotated about a third axis 127. The adjustable arm support 105 can include a fourth joint 121, which can provide a fourth degree of freedom (translation) for the adjustable arm support 105 along a fourth axis 129.

Figure 14:
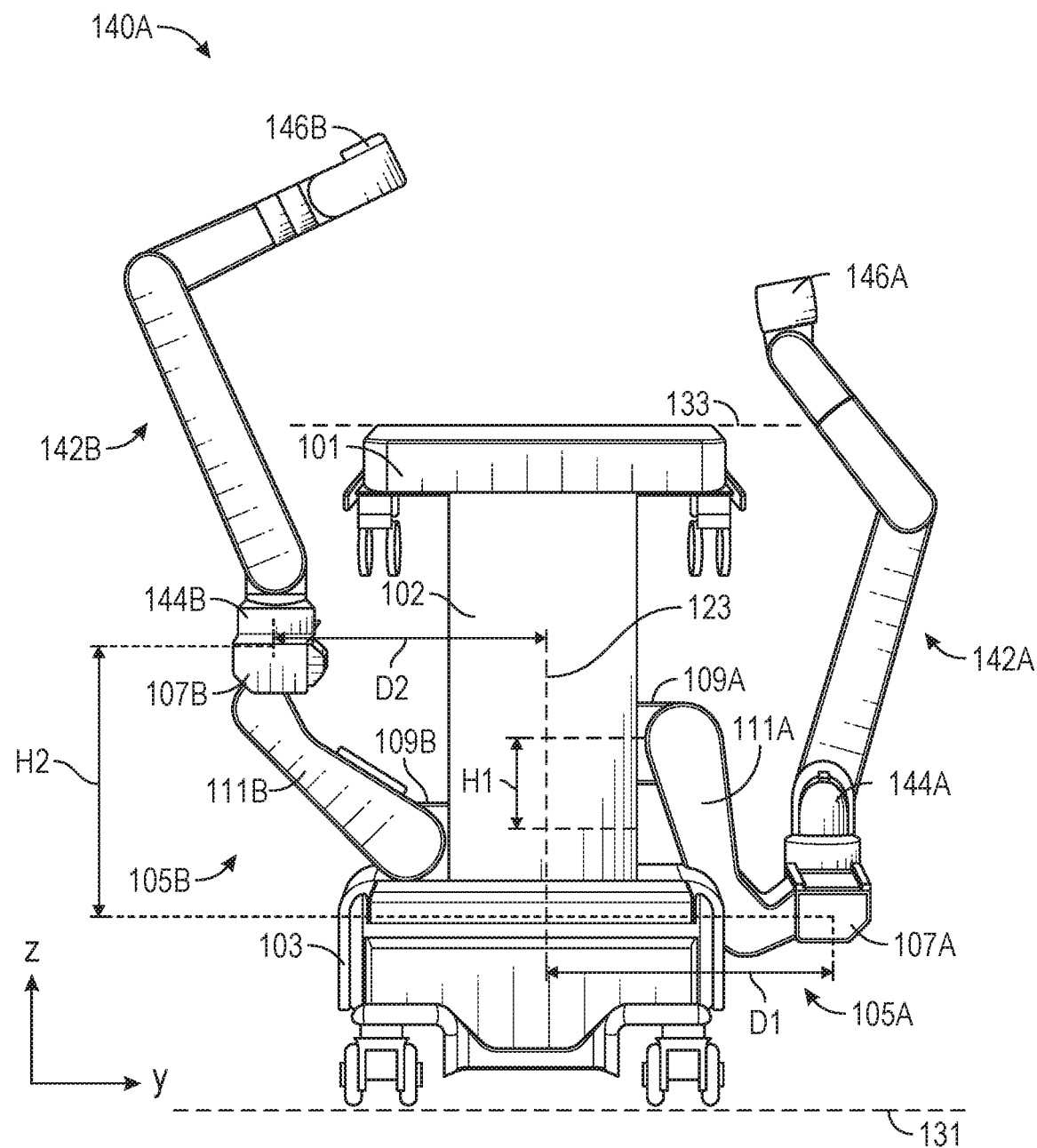
FIG. 14 illustrates an end view of a table-based robotic system with robotic arms attached thereto.

FIG. 14 illustrates an end view of the surgical robotics system 140A with two adjustable arm supports 105A, 105B mounted on opposite sides of a table 101. A first robotic arm 142A is attached to the bar or rail 107A of the first adjustable arm support 105B. The first robotic arm 142A includes a base 144A attached to the rail 107A. The distal end of the first robotic arm 142A includes an instrument drive mechanism 146A that can attach to one or more robotic medical instruments or tools. Similarly, the second robotic arm 142B includes a base 144B attached to the rail 107B. The distal end of the second robotic arm 142B includes an instrument drive mechanism 146B. The instrument drive mechanism 146B can be configured to attach to one or more robotic medical instruments or tools.

In some embodiments, one or more of the robotic arms 142A, 142B comprises an arm with seven or more degrees of freedom. In some embodiments, one or more of the robotic arms 142A, 142B can include eight degrees of freedom, including an insertion axis (1-degree of freedom including insertion), a wrist (3-degrees of freedom including wrist pitch, yaw and roll), an elbow (1-degree of freedom including elbow pitch), a shoulder (2-degrees of freedom including shoulder pitch and yaw), and base 144A, 144B (1-degree of freedom including translation). In some embodiments, the insertion degree of freedom can be provided by the robotic arm 142A, 142B, while in other embodiments, the instrument itself provides insertion via an instrument-based insertion architecture.

C. Instrument Driver & Interface.

The end effectors of the system's robotic arms comprise (i) an instrument driver (alternatively referred to as "instrument drive mechanism" or "instrument device manipulator") that incorporate electro-mechanical means for actuating the medical instrument and (ii) a removable or detachable medical instrument, which may be devoid of any electro-mechanical components, such as motors. This dichotomy may be driven by the need to sterilize medical instruments used in medical procedures, and the inability to adequately sterilize expensive capital equipment due to their intricate mechanical assemblies and sensitive electronics. Accordingly, the medical instruments may be designed to be detached, removed, and interchanged from the instrument driver (and thus the system) for individual sterilization or disposal by the physician or the physician's staff. In contrast, the instrument drivers need not be changed or sterilized, and may be draped for protection.

Figure 15:
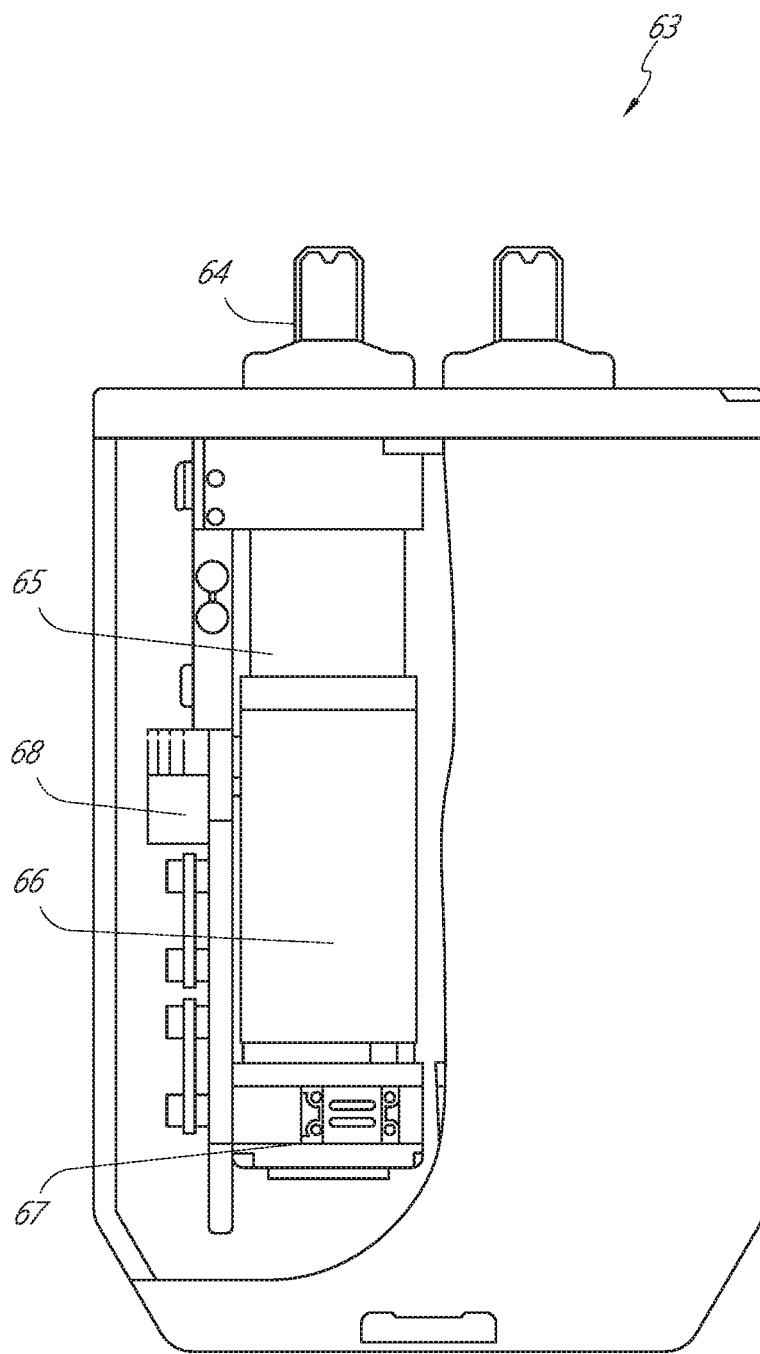
FIG. 15 illustrates an exemplary instrument driver.

FIG. 15 illustrates an example instrument driver. Positioned at the distal end of a robotic arm, instrument driver 62 comprises of one or more drive units 63 arranged with parallel axes to provide controlled torque to a medical instrument via drive shafts 64. Each drive unit 63 comprises an individual drive shaft 64 for interacting with the instrument, a gear head 65 for converting the motor shaft rotation to a desired torque, a motor 66 for generating the drive torque, an encoder 67 to measure the speed of the motor shaft and provide feedback to the control circuitry, and control circuitry 68 for receiving control signals and actuating the drive unit. Each drive unit 63 being independent controlled and motorized, the instrument driver 62 may provide multiple (e.g., four as shown in FIG. 15) independent drive outputs to the medical instrument. In operation, the control circuitry 68 would receive a control signal, transmit a motor signal to the motor 66, compare the resulting motor speed as measured by the encoder 67 with the desired speed, and modulate the motor signal to generate the desired torque.

For procedures that require a sterile environment, the robotic system may incorporate a drive interface, such as a sterile adapter connected to a sterile drape, that sits between the instrument driver and the medical instrument. The chief purpose of the sterile adapter is to transfer angular motion from the drive shafts of the instrument driver to the drive inputs of the instrument while maintaining physical separation, and thus sterility, between the drive shafts and drive inputs. Accordingly, an example sterile adapter may comprise of a series of rotational inputs and outputs intended to be mated with the drive shafts of the instrument driver and drive inputs on the instrument. Connected to the sterile adapter, the sterile drape, comprised of a thin, flexible material such as transparent or translucent plastic, is designed to cover the capital equipment, such as the instrument driver, robotic arm, and cart (in a cart-based system) or table (in a table-based system). Use of the drape would allow the capital equipment to be positioned proximate to the patient while still being located in an area not requiring sterilization (i.e., non-sterile field). On the other side of the sterile drape, the medical instrument may interface with the patient in an area requiring sterilization (i.e., sterile field).

D. Medical Instrument.

Figure 16:
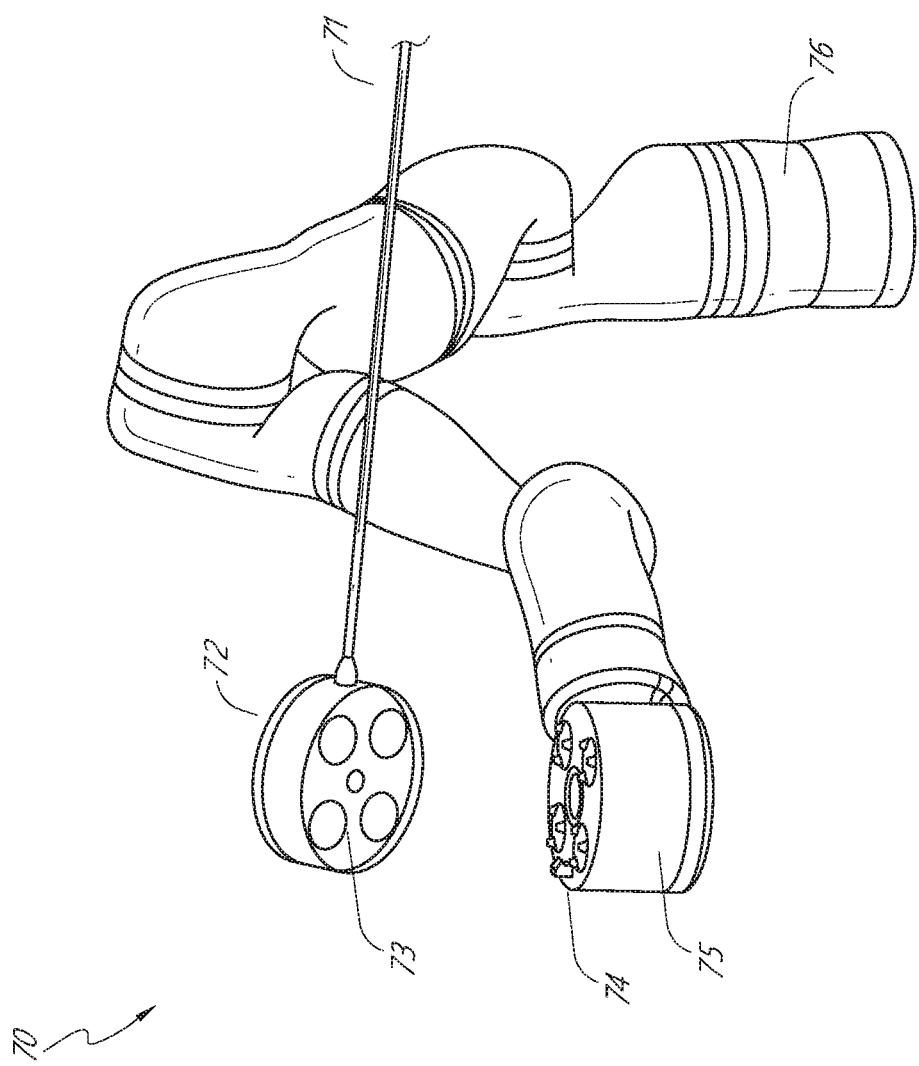
FIG. 16 illustrates an exemplary medical instrument with a paired instrument driver.

FIG. 16 illustrates an example medical instrument with a paired instrument driver. Like other instruments designed for use with a robotic system, medical instrument 70 comprises an elongated shaft 71 (or elongate body) and an instrument base 72. The instrument base 72, also referred to as an "instrument handle" due to its intended design for manual interaction by the physician, may generally comprise rotatable drive inputs 73, e.g., receptacles, pulleys or spools, that are designed to be mated with drive outputs 74 that extend through a drive interface on instrument driver 75 at the distal end of robotic arm 76. When physically connected, latched, and/or coupled, the mated drive inputs 73 of instrument base 72 may share axes of rotation with the drive outputs 74 in the instrument driver 75 to allow the transfer of torque from drive outputs 74 to drive inputs 73. In some embodiments, the drive outputs 74 may comprise splines that are designed to mate with receptacles on the drive inputs 73.

The elongated shaft 71 is designed to be delivered through either an anatomical opening or lumen, e.g., as in endoscopy, or a minimally invasive incision, e.g., as in laparoscopy. The elongated shaft 71 may be either flexible (e.g., having properties similar to an endoscope) or rigid (e.g., having properties similar to a laparoscope) or contain a customized combination of both flexible and rigid portions. When designed for laparoscopy, the distal end of a rigid elongated shaft may be connected to an end effector extending from a jointed wrist formed from a clevis with at least one degree of freedom and a surgical tool or medical instrument, such as, for example, a grasper or scissors, that may be actuated based on force from the tendons as the drive inputs rotate in response to torque received from the drive outputs 74 of the instrument driver 75. When designed for endoscopy, the distal end of a flexible elongated shaft may include a steerable or controllable bending section that may be articulated and bent based on torque received from the drive outputs 74 of the instrument driver 75.

Torque from the instrument driver 75 is transmitted down the elongated shaft 71 using tendons along the shaft 71. These individual tendons, such as pull wires, may be individually anchored to individual drive inputs 73 within the instrument handle 72. From the handle 72, the tendons are directed down one or more pull lumens along the elongated shaft 71 and anchored at the distal portion of the elongated shaft 71, or in the wrist at the distal portion of the elongated shaft. During a surgical procedure, such as a laparoscopic, endoscopic or hybrid procedure, these tendons may be coupled to a distally mounted end effector, such as a wrist, grasper, or scissor. Under such an arrangement, torque exerted on drive inputs 73 would transfer tension to the tendon, thereby causing the end effector to actuate in some way. In some embodiments, during a surgical procedure, the tendon may cause a joint to rotate about an axis, thereby causing the end effector to move in one direction or another. Alternatively, the tendon may be connected to one or more jaws of a grasper at distal end of the elongated shaft 71, where tension from the tendon cause the grasper to close.

In endoscopy, the tendons may be coupled to a bending or articulating section positioned along the elongated shaft 71 (e.g., at the distal end) via adhesive, control ring, or other mechanical fixation. When fixedly attached to the distal end of a bending section, torque exerted on drive inputs 73 would be transmitted down the tendons, causing the softer, bending section (sometimes referred to as the articulable section or region) to bend or articulate. Along the non-bending sections, it may be advantageous to spiral or helix the individual pull lumens that direct the individual tendons along (or inside) the walls of the endoscope shaft to balance the radial forces that result from tension in the pull wires. The angle of the spiraling and/or spacing there between may be altered or engineered for specific purposes, wherein tighter spiraling exhibits lesser shaft compression under load forces, while lower amounts of spiraling results in greater shaft compression under load forces, but also exhibits limits bending. On the other end of the spectrum, the pull lumens may be directed parallel to the longitudinal axis of the elongated shaft 71 to allow for controlled articulation in the desired bending or articulable sections.

In endoscopy, the elongated shaft 71 houses a number of components to assist with the robotic procedure. The shaft may comprise of a working channel for deploying surgical tools (or medical instruments), irrigation, and/or aspiration to the operative region at the distal end of the shaft 71. The shaft 71 may also accommodate wires and/or optical fibers to transfer signals to/from an optical assembly at the distal tip, which may include of an optical camera. The shaft 71 may also accommodate optical fibers to carry light from proximally-located light sources, such as light emitting diodes, to the distal end of the shaft.

At the distal end of the instrument 70, the distal tip may also comprise the opening of a working channel for delivering tools for diagnostic and/or therapy, irrigation, and aspiration to an operative site. The distal tip may also include a port for a camera, such as a fiberscope or a digital camera, to capture images of an internal anatomical space. Relatedly, the distal tip may also include ports for light sources for illuminating the anatomical space when using the camera.

In the example of FIG. 16, the drive shaft axes, and thus the drive input axes, are orthogonal to the axis of the elongated shaft. This arrangement, however, complicates roll capabilities for the elongated shaft 71. Rolling the elongated shaft 71 along its axis while keeping the drive inputs 73 static results in undesirable tangling of the tendons as they extend off the drive inputs 73 and enter pull lumens within the elongated shaft 71. The resulting entanglement of such tendons may disrupt any control algorithms intended to predict movement of the flexible elongated shaft during an endoscopic procedure.

Figure 17:
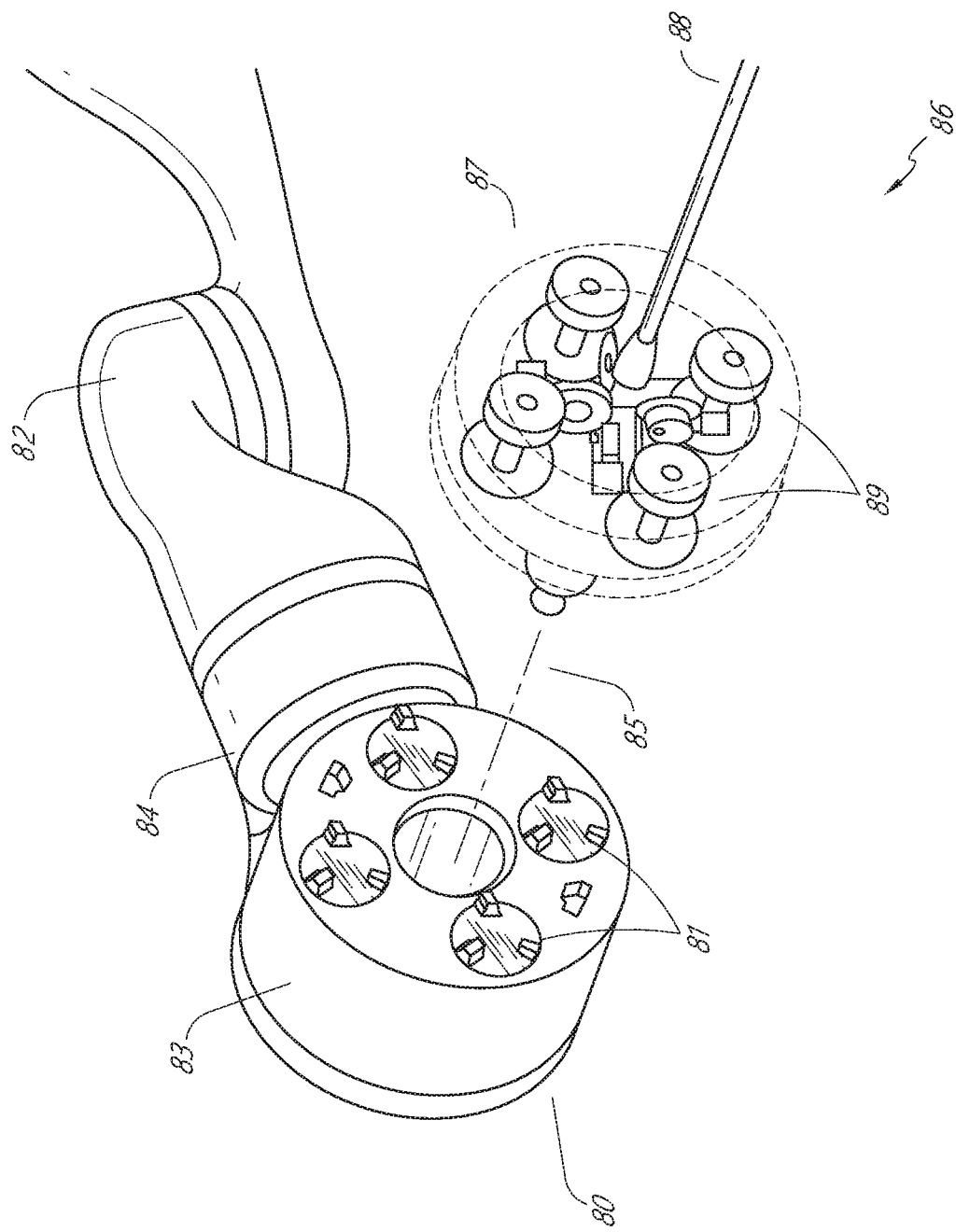
FIG. 17 illustrates an alternative design for an instrument driver and instrument where the axes of the drive units are parallel to the axis of the elongated shaft of the instrument.

FIG. 17 illustrates an alternative design for an instrument driver and instrument where the axes of the drive units are parallel to the axis of the elongated shaft of the instrument. As shown, a circular instrument driver 80 comprises four drive units with their drive outputs 81 aligned in parallel at the end of a robotic arm 82. The drive units, and their respective drive outputs 81, are housed in a rotational assembly 83 of the instrument driver 80 that is driven by one of the drive units within the assembly 83. In response to torque provided by the rotational drive unit, the rotational assembly 83 rotates along a circular bearing that connects the rotational assembly 83 to the non-rotational portion 84 of the instrument driver. Power and controls signals may be communicated from the non-rotational portion 84 of the instrument driver 80 to the rotational assembly 83 through electrical contacts may be maintained through rotation by a brushed slip ring connection (not shown). In other embodiments, the rotational assembly 83 may be responsive to a separate drive unit that is integrated into the non-rotatable portion 84, and thus not in parallel to the other drive units. The rotational mechanism 83 allows the instrument driver 80 to rotate the drive units, and their respective drive outputs 81, as a single unit around an instrument driver axis 85.

Like earlier disclosed embodiments, an instrument 86 may comprise an elongated shaft portion 88 and an instrument base 87 (shown with a transparent external skin for discussion purposes) comprising a plurality of drive inputs 89 (such as receptacles, pulleys, and spools) that are configured to receive the drive outputs 81 in the instrument driver 80. Unlike prior disclosed embodiments, instrument shaft 88 extends from the center of instrument base 87 with an axis substantially parallel to the axes of the drive inputs 89, rather than orthogonal as in the design of FIG. 16.

When coupled to the rotational assembly 83 of the instrument driver 80, the medical instrument 86, comprising instrument base 87 and instrument shaft 88, rotates in combination with the rotational assembly 83 about the instrument driver axis 85. Since the instrument shaft 88 is positioned at the center of instrument base 87, the instrument shaft 88 is coaxial with instrument driver axis 85 when attached. Thus, rotation of the rotational assembly 83 causes the instrument shaft 88 to rotate about its own longitudinal axis. Moreover, as the instrument base 87 rotates with the instrument shaft 88, any tendons connected to the drive inputs 89 in the instrument base 87 are not tangled during rotation. Accordingly, the parallelism of the axes of the drive outputs 81, drive inputs 89, and instrument shaft 88 allows for the shaft rotation without tangling any control tendons.

Figure 18:
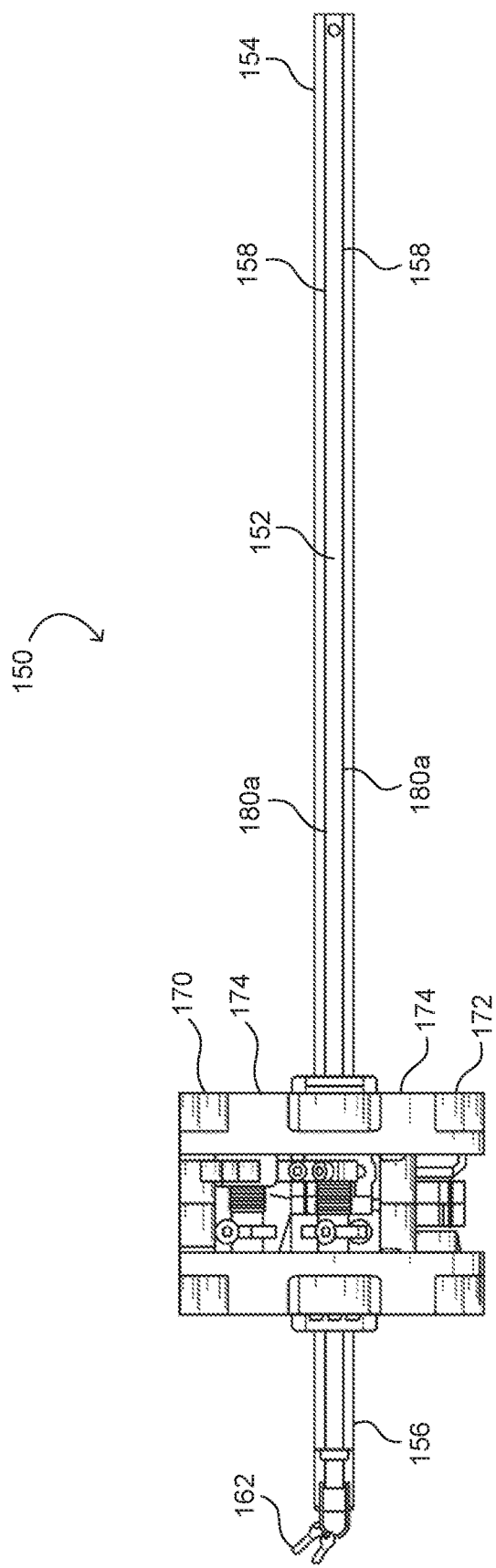
FIG. 18 illustrates an instrument having an instrument-based insertion architecture.

FIG. 18 illustrates an instrument having an instrument based insertion architecture in accordance with some embodiments. The instrument 150 can be coupled to any of the instrument drivers discussed above. The instrument 150 comprises an elongated shaft 152, an end effector 162 connected to the shaft 152, and a handle 170 coupled to the shaft 152. The elongated shaft 152 comprises a tubular member having a proximal portion 154 and a distal portion 156. The elongated shaft 152 comprises one or more channels or grooves 158 along its outer surface. The grooves 158 are configured to receive one or more wires or cables 180 therethrough. One or more cables 180 thus run along an outer surface of the elongated shaft 152. In other embodiments, cables 180 can also run through the elongated shaft 152. Manipulation of the one or more cables 180 (e.g., via an instrument driver) results in actuation of the end effector 162.

The instrument handle 170, which may also be referred to as an instrument base, may generally comprise an attachment interface 172 having one or more mechanical inputs 174, e.g., receptacles, pulleys or spools, that are designed to be reciprocally mated with one or more torque couplers on an attachment surface of an instrument driver.

In some embodiments, the instrument 150 comprises a series of pulleys or cables that enable the elongated shaft 152 to translate relative to the handle 170. In other words, the instrument 150 itself comprises an instrument-based insertion architecture that accommodates insertion of the instrument, thereby minimizing the reliance on a robot arm to provide insertion of the instrument 150. In other embodiments, a robotic arm can be largely responsible for instrument insertion.

E. Controller.

Any of the robotic systems described herein can include an input device or controller for manipulating an instrument attached to a robotic arm. In some embodiments, the controller can be coupled (e.g., communicatively, electronically, electrically, wirelessly and/or mechanically) with an instrument such that manipulation of the controller causes a corresponding manipulation of the instrument e.g., via master slave control.

Figure 19:
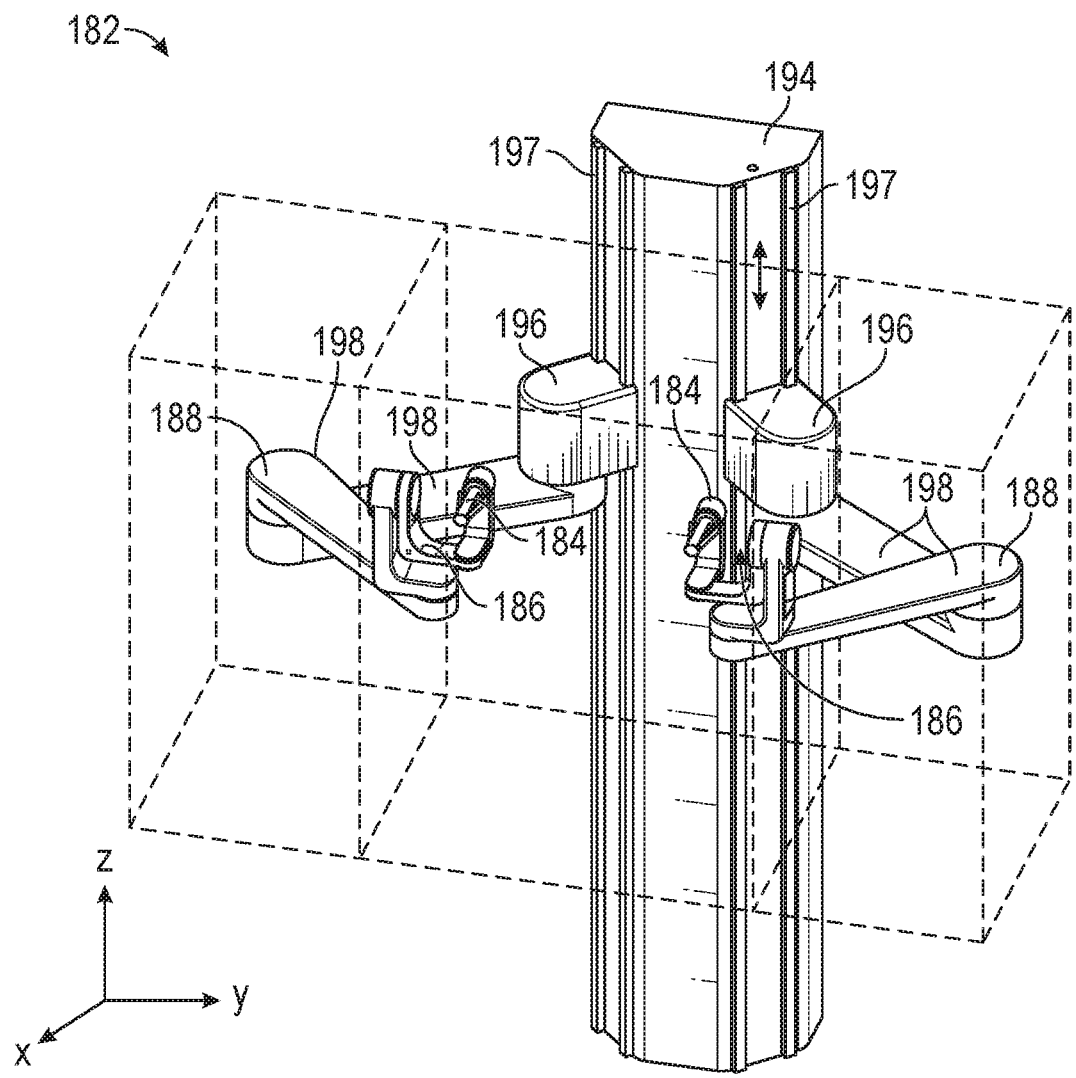
FIG. 19 illustrates an exemplary controller.

FIG. 19 is a perspective view of an embodiment of a controller 182. In the present embodiment, the controller 182 comprises a hybrid controller that can have both impedance and admittance control. In other embodiments, the controller 182 can utilize just impedance or passive control. In other embodiments, the controller 182 can utilize just admittance control. By being a hybrid controller, the controller 182 advantageously can have a lower perceived inertia while in use.

In the illustrated embodiment, the controller 182 is configured to allow manipulation of two medical instruments, and includes two handles 184. Each of the handles 184 is connected to a gimbal 186. Each gimbal 186 is connected to a positioning platform 188.

As shown in FIG. 19, each positioning platform 188 includes a SCARA arm (selective compliance assembly robot arm) 198 coupled to a column 194 by a prismatic joint 196. The prismatic joints 196 are configured to translate along the column 194 (e.g., along rails 197) to allow each of the handles 184 to be translated in the z-direction, providing a first degree of freedom. The SCARA arm 198 is configured to allow motion of the handle 184 in an x-y plane, providing two additional degrees of freedom.

In some embodiments, one or more load cells are positioned in the controller. For example, in some embodiments, a load cell (not shown) is positioned in the body of each of the gimbals 186. By providing a load cell, portions of the controller 182 are capable of operating under admittance control, thereby advantageously reducing the perceived inertia of the controller while in use. In some embodiments, the positioning platform 188 is configured for admittance control, while the gimbal 186 is configured for impedance control. In other embodiments, the gimbal 186 is configured for admittance control, while the positioning platform 188 is configured for impedance control. Accordingly, for some embodiments, the translational or positional degrees of freedom of the positioning platform 188 can rely on admittance control, while the rotational degrees of freedom of the gimbal 186 rely on impedance control.

F. Navigation and Control.

Traditional endoscopy may involve the use of fluoroscopy (e.g., as may be delivered through a C-arm) and other forms of radiation-based imaging modalities to provide endoluminal guidance to an operator physician. In contrast, the robotic systems contemplated by this disclosure can provide for non-radiation-based navigational and localization means to reduce physician exposure to radiation and reduce the amount of equipment within the operating room. As used herein, the term "localization" may refer to determining and/or monitoring the position of objects in a reference coordinate system. Technologies such as pre-operative mapping, computer vision, real-time EM tracking, and robot command data may be used individually or in combination to achieve a radiation-free operating environment. In other cases, where radiation-based imaging modalities are still used, the pre-operative mapping, computer vision, real-time EM tracking, and robot command data may be used individually or in combination to improve upon the information obtained solely through radiation-based imaging modalities.

Figure 20:
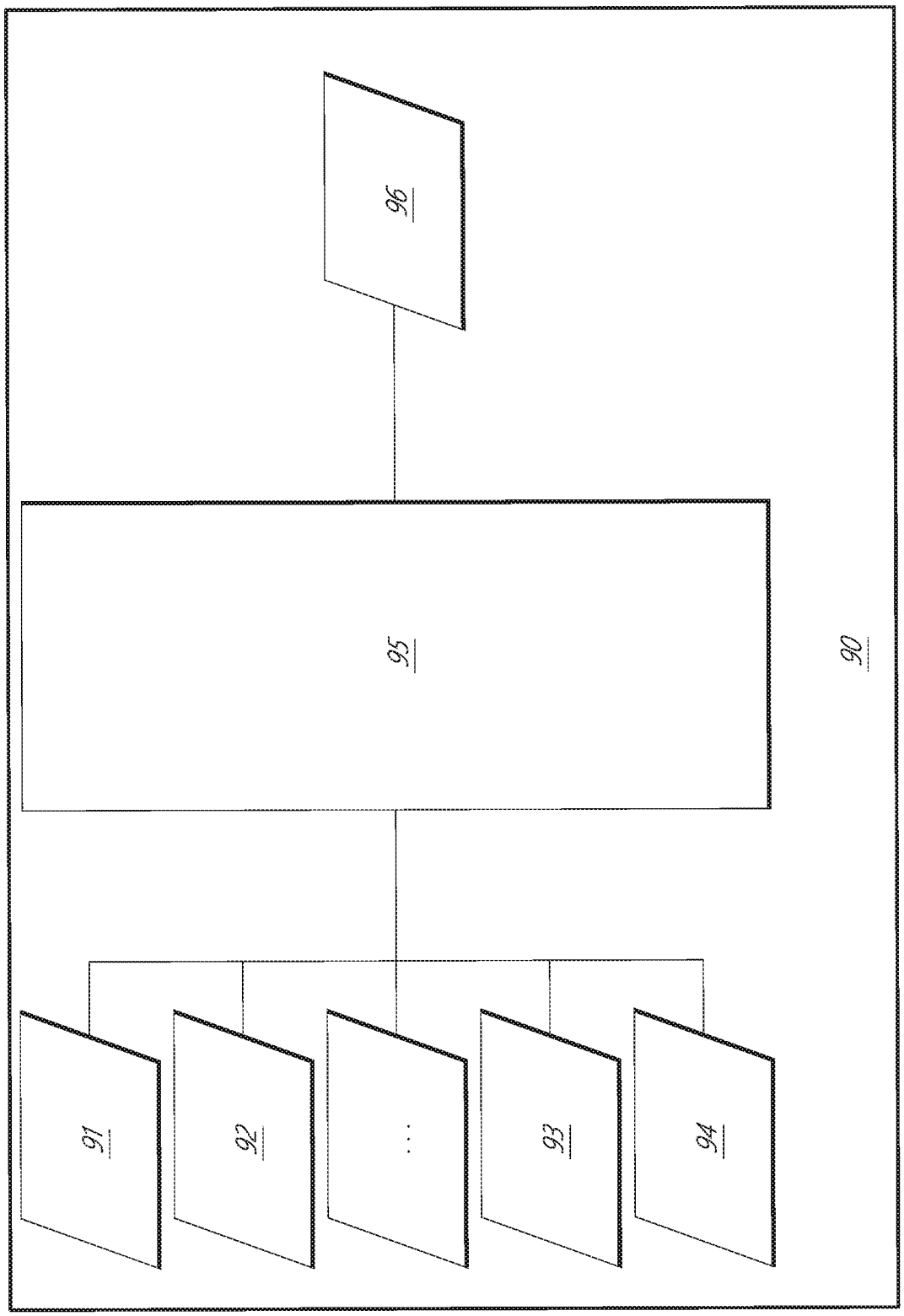
FIG. 20 depicts a block diagram illustrating a localization system that estimates a location of one or more elements of the robotic systems of FIGS. 1-10, such as the location of the instrument of FIGS. 16-18, in accordance to an example embodiment.

FIG. 20 is a block diagram illustrating a localization system 90 that estimates a location of one or more elements of the robotic system, such as the location of the instrument, in accordance to an example embodiment. The localization system 90 may be a set of one or more computer devices configured to execute one or more instructions. The computer devices may be embodied by a processor (or processors) and computer-readable memory in one or more components discussed above. By way of example and not limitation, the computer devices may be in the tower 30 shown in FIG. 1, the cart shown in FIGS. 1-4, the beds shown in FIGS. 5-14, etc.

As shown in FIG. 20, the localization system 90 may include a localization module 95 that processes input data 91-94 to generate location data 96 for the distal tip of a medical instrument. The location data 96 may be data or logic that represents a location and/or orientation of the distal end of the instrument relative to a frame of reference. The frame of reference can be a frame of reference relative to the anatomy of the patient or to a known object, such as an EM field generator (see discussion below for the EM field generator).

The various input data 91-94 are now described in greater detail. Pre-operative mapping may be accomplished through the use of the collection of low dose CT scans. Pre-operative CT scans are reconstructed into three-dimensional images, which are visualized, e.g. as "slices" of a cutaway view of the patient's internal anatomy. When analyzed in the aggregate, image-based models for anatomical cavities, spaces and structures of the patient's anatomy, such as a patient lung network, may be generated. Techniques such as center-line geometry may be determined and approximated from the CT images to develop a three-dimensional volume of the patient's anatomy, referred to as model data 91 (also referred to as "preoperative model data" when generated using only preoperative CT scans). The use of center-line geometry is discussed in U.S. patent application Ser. No. 14/523,760, the contents of which are herein incorporated in its entirety. Network topological models may also be derived from the CT-images, and are particularly appropriate for bronchoscopy.

In some embodiments, the instrument may be equipped with a camera to provide vision data 92. The localization module 95 may process the vision data to enable one or more vision-based location tracking. For example, the preoperative model data may be used in conjunction with the vision data 92 to enable computer vision-based tracking of the medical instrument (e.g., an endoscope or an instrument advance through a working channel of the endoscope). For example, using the preoperative model data 91, the robotic system may generate a library of expected endoscopic images from the model based on the expected path of travel of the endoscope, each image linked to a location within the model. Intra-operatively, this library may be referenced by the robotic system in order to compare real-time images captured at the camera (e.g., a camera at a distal end of the endoscope) to those in the image library to assist localization.

Other computer vision-based tracking techniques use feature tracking to determine motion of the camera, and thus the endoscope. Some features of the localization module 95 may identify circular geometries in the preoperative model data 91 that correspond to anatomical lumens and track the change of those geometries to determine which anatomical lumen was selected, as well as the relative rotational and/or translational motion of the camera. Use of a topological map may further enhance vision-based algorithms or techniques.

Optical flow, another computer vision-based technique, may analyze the displacement and translation of image pixels in a video sequence in the vision data 92 to infer camera movement. Examples of optical flow techniques may include motion detection, object segmentation calculations, luminance, motion compensated encoding, stereo disparity measurement, etc. Through the comparison of multiple frames over multiple iterations, movement and location of the camera (and thus the endoscope) may be determined.

The localization module 95 may use real-time EM tracking to generate a real-time location of the endoscope in a global coordinate system that may be registered to the patient's anatomy, represented by the preoperative model. In EM tracking, an EM sensor (or tracker) comprising of one or more sensor coils embedded in one or more locations and orientations in a medical instrument (e.g., an endoscopic tool) measures the variation in the EM field created by one or more static EM field generators positioned at a known location. The location information detected by the EM sensors is stored as EM data 93. The EM field generator (or transmitter), may be placed close to the patient to create a low intensity magnetic field that the embedded sensor may detect. The magnetic field induces small currents in the sensor coils of the EM sensor, which may be analyzed to determine the distance and angle between the EM sensor and the EM field generator. These distances and orientations may be intra-operatively "registered" to the patient anatomy (e.g., the preoperative model) in order to determine the geometric transformation that aligns a single location in the coordinate system with a position in the pre-operative model of the patient's anatomy. Once registered, an embedded EM tracker in one or more positions of the medical instrument (e.g., the distal tip of an endoscope) may provide real-time indications of the progression of the medical instrument through the patient's anatomy.

Robotic command and kinematics data 94 may also be used by the localization module 95 to provide localization data 96 for the robotic system. Device pitch and yaw resulting from articulation commands may be determined during pre-operative calibration. Intra-operatively, these calibration measurements may be used in combination with known insertion depth information to estimate the position of the instrument. Alternatively, these calculations may be analyzed in combination with EM, vision, and/or topological modeling to estimate the position of the medical instrument within the network.

As FIG. 20 shows, a number of other input data can be used by the localization module 95. For example, although not shown in FIG. 20, an instrument utilizing shape-sensing fiber can provide shape data that the localization module 95 can use to determine the location and shape of the instrument.

The localization module 95 may use the input data 91-94 in combination(s). In some cases, such a combination may use a probabilistic approach where the localization module 95 assigns a confidence weight to the location determined from each of the input data 91-94. Thus, where the EM data may not be reliable (as may be the case where there is EM interference) the confidence of the location determined by the EM data 93 can be decrease and the localization module 95 may rely more heavily on the vision data 92 and/or the robotic command and kinematics data 94.

As discussed above, the robotic systems discussed herein may be designed to incorporate a combination of one or more of the technologies above. The robotic system's computer-based control system, based in the tower, bed and/or cart, may store computer program instructions, for example, within a non-transitory computer-readable storage medium such as a persistent magnetic storage drive, solid state drive, or the like, that, upon execution, cause the system to receive and analyze sensor data and user commands, generate control signals throughout the system, and display the navigational and localization data, such as the position of the instrument within the global coordinate system, anatomical map, etc.

2. Introduction to Medical Instruments that Include Optical Fiber(s).

Aspects of this disclosure relate to medical instruments which may include one or more optical fibers. Each of the optical fibers may be configured to sense strain along the length of the fiber. Strain data can be used for a number of different applications, including sensing the shape of the optical fiber (as well as the medical instrument containing the optical fiber), testing the strain of medical instrument design during development of a new medical instrument, etc.

Figure 21:
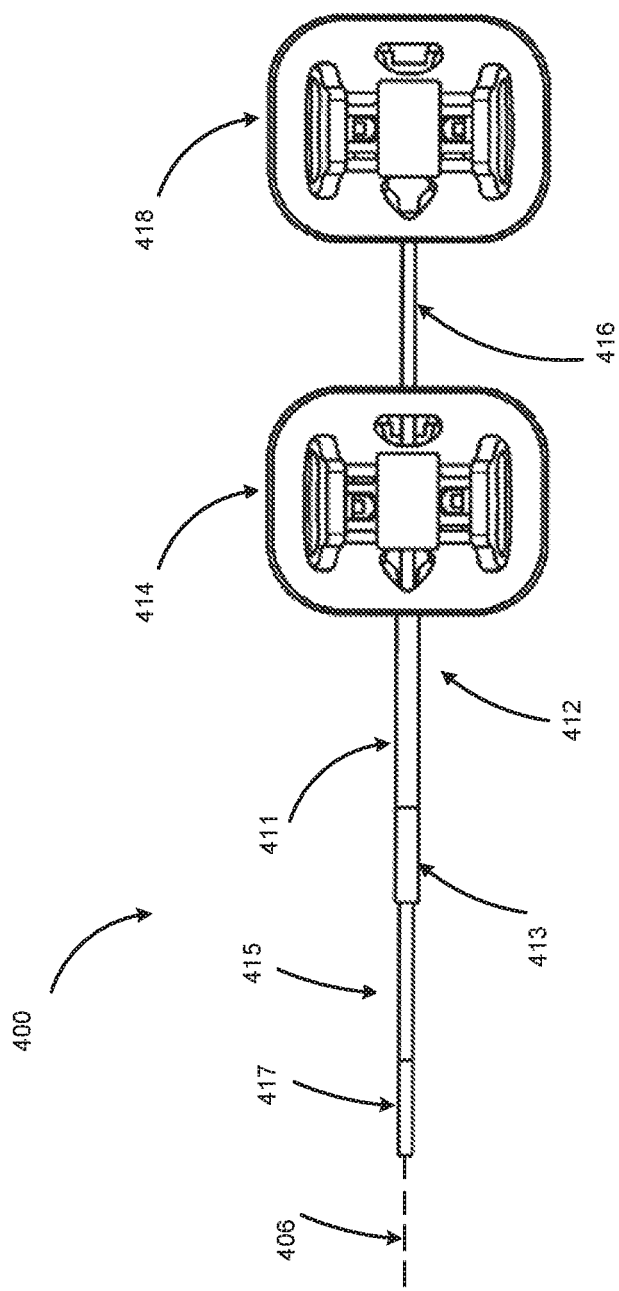
FIG. 21 shows a top view of an example medical instrument having two telescoping flexible instruments in accordance with aspects of this disclosure.

FIG. 21 shows a top view of an example medical instrument 400 (e.g., an endoscope) comprising at least two telescoping flexible instruments, such as an inner leader portion 415 (referred to herein as the "leader") and an outer sheath portion 411 (referred to herein as the "sheath"), in accordance with aspects of this disclosure. The medical instrument 400 can include the leader 415 tubular component nested or partially nested inside and longitudinally-aligned with the sheath 411 tubular component. In some embodiments, the medical instrument 400 can be embodied as an endoscope, for example, comprising one or more optical sensors or cameras at a distal end of the endoscope. The sheath 411 includes a proximal sheath section 412 and distal sheath section 413. The leader 415 has a smaller outer diameter than the sheath 411 and includes a proximal leader section 416 and distal leader section 417. A sheath base 414 and a leader base 418 are configured to actuate the distal sheath section 413 and the distal leader section 417, respectively, for example, based on control signals from a user of a surgical robotic system (e.g., robotically-enabled system 10, or one of the robotic medical systems 200, 300, or 400) or associated system(s). The sheath base 414 and the leader base 418 may be part of, e.g., the instrument driver 62 shown in FIG. 15.

Both the sheath base 414 and the leader base 418 include drive mechanisms (e.g., the drive units 63 described with reference to FIG. 15) to control pull wires coupled to the sheath 411 and leader 415. For example, the sheath base 414 generates tensile loads on pull wires coupled to the sheath 411 to deflect the distal sheath section 413. Similarly, the leader base 418 generates tensile loads on pull wires coupled to the leader 415 to deflect the distal leader section 417. Both the sheath base 414 and leader base 418 may also include couplings for the routing of pneumatic pressure, electrical power, electrical signals, and/or optical signals from instrument drivers to the sheath 411 and leader 414, respectively. A pull wire may pass through a steel coil pipe arranged along the length of the pull wire within the sheath 411 or the leader 415, which transfers axial compression back to the origin of the load, e.g., the sheath base 414 or the leader base 418, respectively.

The medical instrument 400 can navigate through the anatomy of a patient due in part to the multiple degrees of freedom provided by the pull wires coupled to the sheath 411 and the leader 415. For example, four or more pull wires may be used in either the sheath 411 and/or the leader 415, providing eight or more degrees of freedom. In other embodiments, up to three pull wires may be used, providing up to six degrees of freedom. The sheath 411 and leader 415 may be rotated up to 360 degrees along a longitudinal axis 406, providing more degrees of freedom. The combination of rotational angles and multiple degrees of freedom provides a user of the surgical robotic system 100 with a user friendly and instinctive control of the medical instrument 400. Although not illustrated in FIG. 21, the medical instrument 400 may include one or more optical fibers for sensing the shape in one or more portions of the medical instrument 400. For example, as the optical fiber(s) can be included in the leader portion of the medical instrument 400 (as described in further detail below with reference to FIG. 22). Alternatively or additionally, the optical fiber(s) can be included in the sheath portion of the medical instrument 400. As will be explained in more detail below, information from the optical fibers can be used in combination with information from other input sources, such as other input sensors, modelling data, known properties and characteristics of the endoscope, and the like, to enhance performance of the navigation system, catheter control, or the like.

Figure 22:
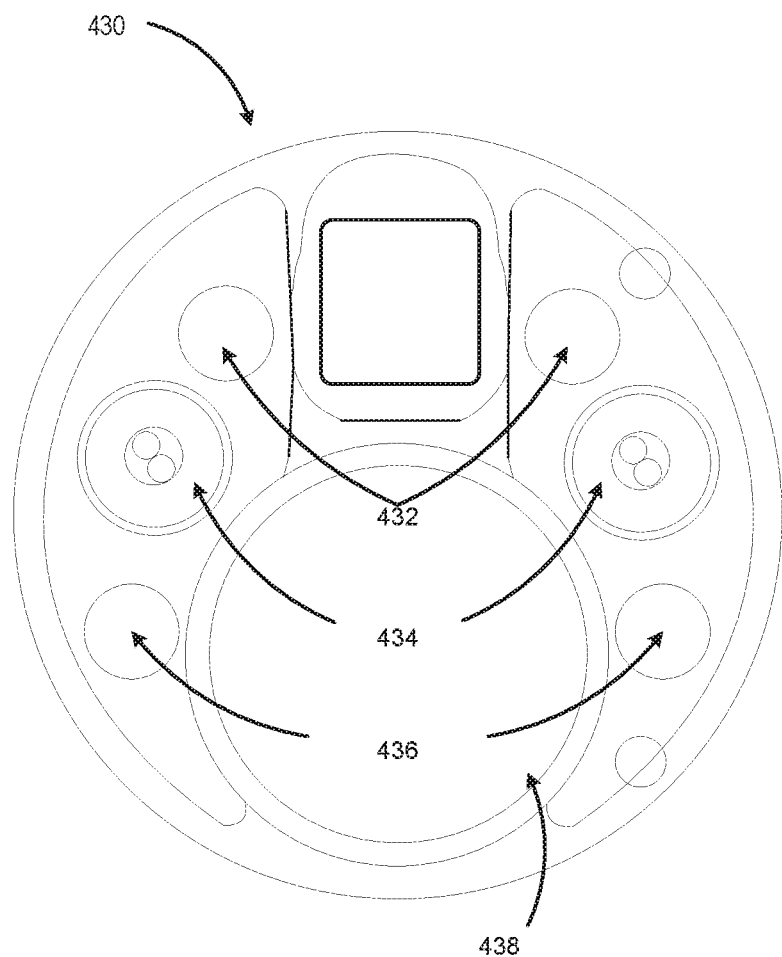
FIG. 22 illustrates an example cross-section of a portion of the medical instrument shown in FIG. 21 in accordance with aspects of this disclosure.

FIG. 22 illustrates an example cross-section 430 of the medical instrument 400 shown in FIG. 21 in accordance with aspects of this disclosure. In FIG. 22, the cross-section 430 is taken through the leader 415 and shows illumination sources 432, electromagnetic (EM) coils 434, and fibers 436. The illumination sources 432 provide light to illuminate an interior portion of an anatomical space. The provided light may allow an imaging device located at the tip of the medical instrument 400 to record images of the anatomical space, which can then be transmitted to a computer system, such as, e.g., the console 31, for processing as described herein. EM coils 434 may be used with an EM tracking system to detect the position and orientation of the tip of the medical instrument 400 while disposed within an anatomical system. The cross-section 430 further shows a working channel 438 through which surgical instruments, such as, e.g., biopsy needles, may be inserted through the shaft of the leader 415, allowing access to the area near the distal end of the medical instrument 400.

While the illustrated embodiment is disclosed as including illumination sources 432 and EM coils 434, other embodiments of the medical instruments can be without one or more of such features.

Figure 23:
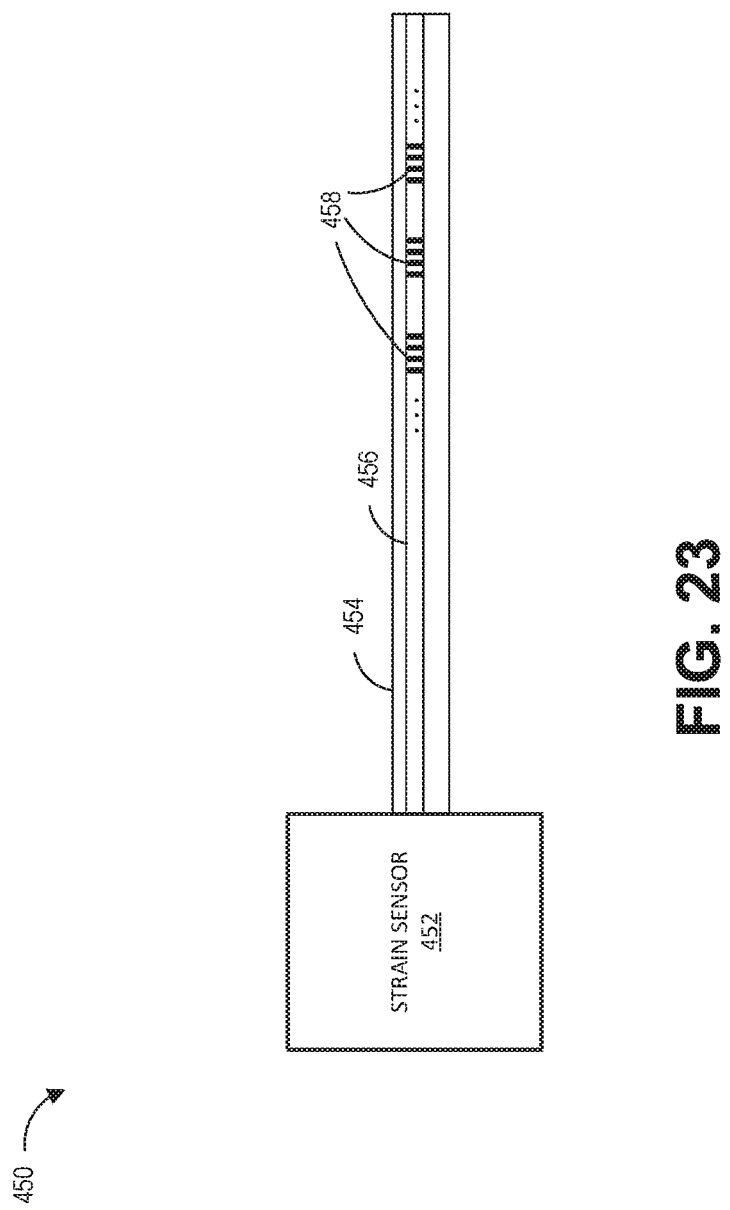
FIG. 23 shows an example system having a strain sensor, which can be used to generate and detect light used for determining strain along the medical instrument in accordance with aspects of this disclosure.

FIG. 23 shows an example system 450 having a strain sensor 452 which can be used to generate and detect light used for determining strain along the medical instrument 400 in accordance with aspects of this disclosure. The optical fiber 456 of a medical instrument 454 can include one or more segments of fiber Bragg gratings (FBGs) 458, which reflect certain wavelengths of light while transmitting other wavelengths. The FBGs 458 may comprise a series of modulations of refractive index so as to generate a spatial periodicity in the refraction index. During fabrication of the FBGs 458, the modulations can be spaced by a known distance, thereby causing reflection of a known band of wavelengths. The strain sensor 452 may transmit light through the optical fiber 456 and receive light reflected from the optical fiber 456. The strain sensor 452 may further generate reflection spectrum data based on the wavelengths of light reflected by the FBGs 458.

As shown in FIG. 23, a single optical fiber may include multiple sets of FBGs 458. The medical instrument 454 may include multiple optical fibers, and the shape detector 452 may detect and analyze signals from more than one fiber. One or more optical fibers may be included in the leader 415 of FIG. 21, the sheath 411 of FIG. 21, or both. Although the instrument 454 is used as an example, the techniques described herein can be applied to any other elongated instrument. The strain sensor 452 may be operatively coupled with a controller configured to determine a geometric shape or configuration of the optical fiber 456 and, therefore, at least a portion of the instrument 454 (or other elongated instrument such as a catheter and the like) based on a spectral analysis of the detected reflected light signals.

In some embodiments, the controller coupled to or in communication with the strain sensor 452 (e.g., robotically-enabled system 10, or one of the robotic medical systems 200, 300, or 400) or associated system(s) can analyze the reflection spectrum data to generate position and orientation data of the instrument 454 in two or three dimensional space. In particular, as the instrument 454 bends, the optical fiber 456 positioned inside the instrument 454 also bends, which causes strain on the optical fiber 456. When strain is induced on the optical fiber 456, the spacing of the modulations of the FBGs 458 will change, depending on the amount of strain on the optical fiber 456. To measure strain, light is sent down the optical fiber 456, and characteristics of the returning light are measured. For example, the FBGs 458 may produce a reflected wavelength that is a function of the strain on the optical fiber 456 (and other factors such as temperature) at the positions of the FBGs 458. Based on the specific wavelengths of light reflected by the FBGs 458, the system can determine the amount of strain on the optical fiber 456. In some embodiments, the system may use the determined strain to predict the shape of the optical fiber 456 (e.g., based on how the strain characteristics of a "straight" medical instrument may differ from those of a "curved" medical instrument). Thus, the system can determine, for example, how many degrees the instrument 454 has bent in one or more directions (e.g., in response to commands from the surgical robotic system 500) by identifying differences in the reflection spectrum data.

The optical fiber(s) 456 are suitable for data collection inside the body of the patient because no line-of-sight to the shape sensing optical fiber is required. Various systems and methods for monitoring the shape and relative position of an optical fiber in three dimensions are described in U.S. Patent Application Publication No. 2006/0013523, filed Jul. 13, 2005, titled "FIBER OPTIC POSITION AND SHAPE SENSING DEVICE AND METHOD RELATING THERETO," and U.S. Pat. No. 6,389,187, filed on Jun. 17, 1998, entitled "OPTICAL FIBER BEND SENSOR," the contents of which are fully incorporated herein by reference.

A. Medical Instruments Using Optical Fiber(s) in Place of Pull Wires.

Although FIGS. 22 and 23 described embodiments in which the medical instrument includes one or more optical fibers and one or more pull wires along the length of the medical instrument, there may be tradeoffs associated with such designs. For example, with reference to FIG. 22, the diameter of the medical instrument 400 may have to be increased in order to accommodate the one or more fibers 436. It may be desirable to save as much space within the cross-section 430 of the medical instrument 400 since a smaller diameter medical instrument 400 may be able to access or fit through smaller lumens within the patient's anatomy, allowing improved access to certain treatment sites.

Pull wires used in medical instruments can be subject to high tension forces in local regions. However, pull wires may be interrogated globally at either end of the wire by using tension sensors (e.g., a torque sensor). The information provided by a tension sensor can only provide tension at the location of the tension sensor, but cannot provide information regarding strain at different locations along the pull wires. Certain techniques for measuring pull wire tension use a torque sensor located on an instrument driver. Torque sensors can only measure the global sum-total of tension on the pull wire, and thus, may not be used to measure localized tension along a pull wire. Additionally, torques sensors can be subject to noise due to electronic signal fluctuations, delays, and additional sources of error due to being collocated on the same axis as the drive motor.

The use of optical fibers to measure strain in place of torque sensors can thus provide more accurate, localized measurement of strain. Certain optical fibers can withstand pull forces (e.g., >30 N), and thus, can be used as pull wires for some medical instruments. One advantage of using optical fibers as pull wires is that the optical fibers can be inscribed with FBGs, which can be used to measure strain at various locations along the pull wires. This advantage lends itself well to understanding the local tension gradients on the optical fiber pull wires based on the properties of the FBGs under tension.

In order to gain the strain sensing benefits of an optical fiber included within a medical instrument (e.g., the medical instrument 400) without substantially increasing the diameter of the medical instrument, one or more of the pulls wires can be replaced with one or more optical fibers—stated differently, the optical fibers may be use as pull wires.

Figure 24:
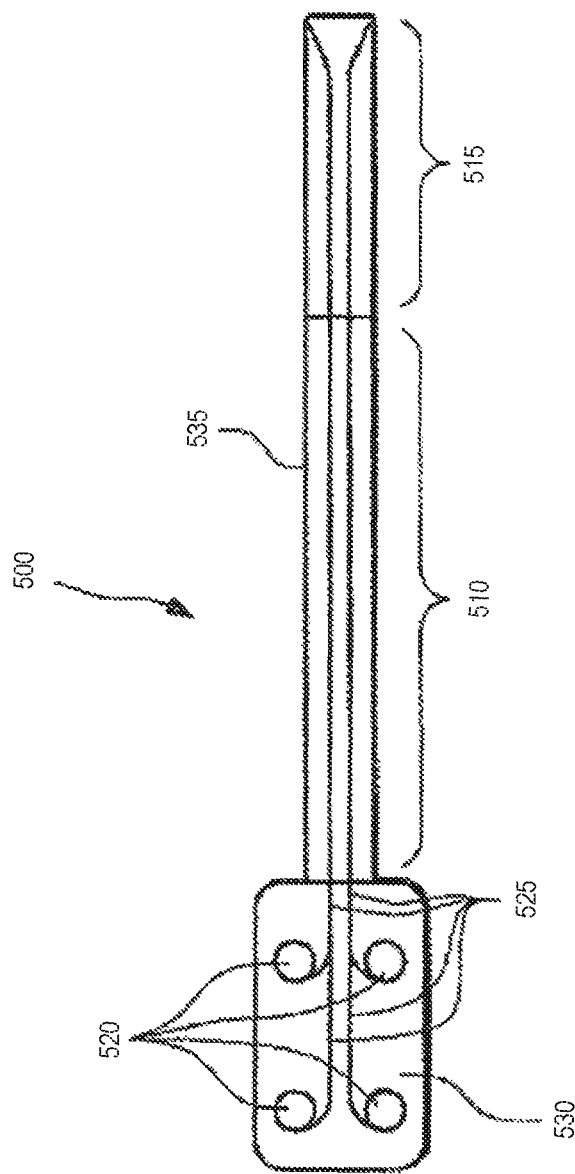
FIG. 24 illustrates an example medical instrument having optical fiber pull wires in accordance with aspects of this disclosure.

FIG. 24 illustrates an example medical instrument 500 having optical fiber pull wires 525 in accordance with aspects of this disclosure. The medical instrument 500 includes a plurality of pull wires 525 extending from an instrument base 530 through an elongated shaft 535. The elongated shaft 535 includes a proximal portion 510 and a distal portion 515. The pull wires 525 may extend from a proximal end of the elongated shaft 535 (e.g., near the instrument base 530) to a distal end of the elongated shaft 535 (e.g., at a distal end of the distal portion 515 of the elongated shaft 535). The pull wires 525 may extend to one or more termination points at the distal portion 515 of the elongated shaft 535. The pull wires 525 are configured to steer or bend the distal portion 515 of the elongated shaft 535 when tensioned in various configurations. The pull wires 535 may be configured to cause actuation of the medical instrument 500 in at least one degree of freedom, for example, each pull wire 525 may be configured to actuate the distal portion 515 of the elongated shaft 535 in a separate degree of freedom. In contrast, the proximal portion 510 may be configured to be stiffer and more resistant to bending or steering than the distal portion 515. The medical instrument 500 can be configured to be inserted into a region of a body (e.g., into a luminal network of patient).

In some embodiments, at least one of the pull wires 525 comprises an optical fiber configured to provide an indication of strain along the pull wire 525. That is, at least one of the pull wires 525 may be formed as optical fibers in place of flexible tendons, or other mechanical structures that allow for steering or deflection of the elongated shaft 535 used in other medical instruments. In the embodiment of FIG. 24, any number of the pull wires 525 may be formed as an optical fiber, to enable strain sensing along the elongated shaft 535.

The instrument base 530 also includes a plurality of proximal axles or spindles 520 configured to interface with an instrument driver (e.g., the instrument drivers 28, 62, and 75 of FIGS. 1, 15, and 16, also referred to as an instrument positioning device). When coupled to a robotic system, the system can drive each of the spindles 520 to produce precise steering or bending movement of the distal portion 515 of the elongated shaft 535. The instrument base 520 can be mounted to an instrument driver, such that a torque can be provided to each of the spindles 520 via a corresponding drive shaft (e.g., drive shaft 64 of FIG. 15) formed on the instrument driver. The instrument driver can be configured to be attached to the medical instrument 500 and control movement of the medical instrument 500 via actuation of the one or more pull wires 525.

The medical instrument 500 may further include an end effector (e.g., the end effector 162 of FIG. 18) at a distal end of the elongated shaft 535. The medical instrument 500 may also include additional pull wires 525 such that the end effector can be actuated by at least one of the pull wires 525.

Figure 25:
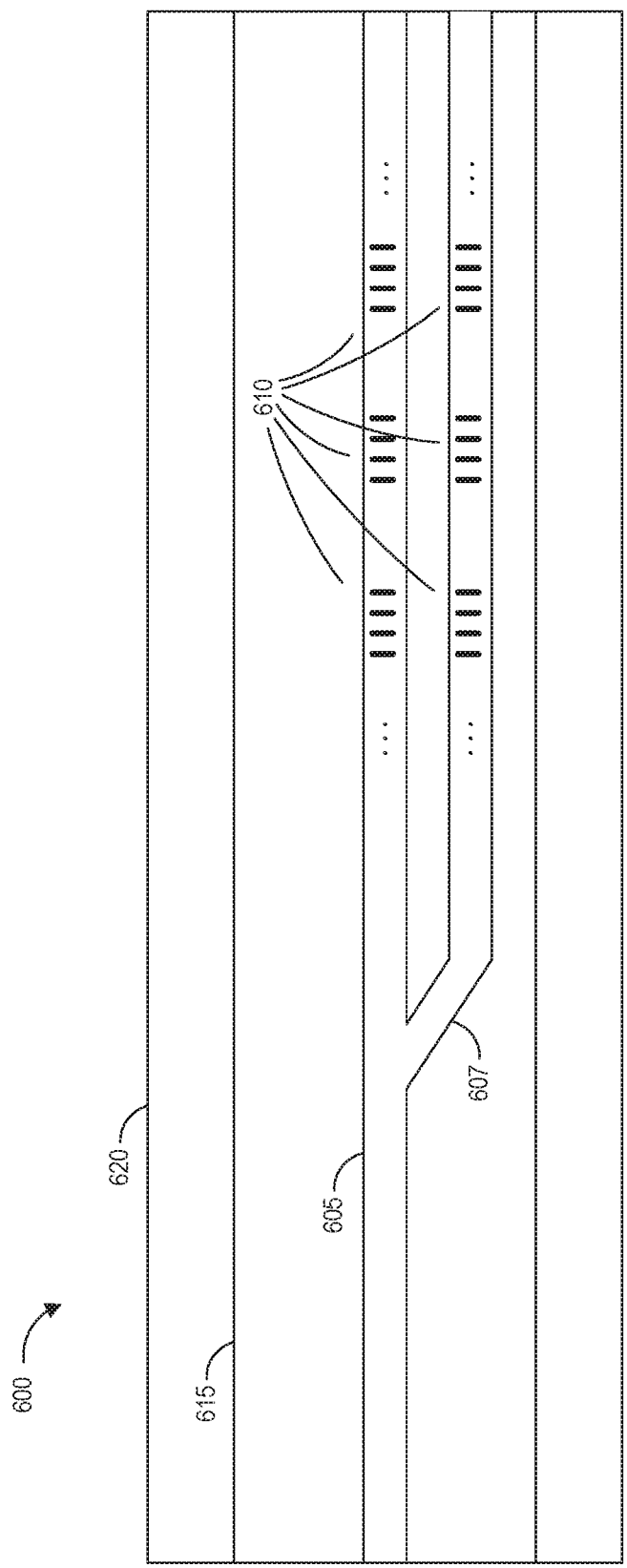
FIG. 25 illustrates an example optical fiber that can be used as a pull wire in accordance with aspects of this disclosure.

FIG. 25 illustrates features of an example optical fiber 600 that can be used as a pull wire in accordance with aspects of this disclosure. The optical fiber 600 includes a core 605, a cladding 615 surrounding the core 605, and a coating 620 surrounding the cladding 615. As shown in FIG. 25, at least one FBG 610 is inscribed in the core 605. The FBG 610 is configured to reflect light at a wavelength indicative of the strain along the optical fiber 600 at a position of the FBG 610.

As described above, the FBG 610 may comprise a series of modulations of refractive index so as to generate a spatial periodicity in the refraction index. During fabrication of the FBGs 610, the modulations can be spaced by a known distance, thereby causing reflection of a known band of wavelengths. Thus, each FBG 610 may be configured to reflect light at a wavelength that is dependent on the distance between the modulations of the refractive index of the core 605. When one of the FBGs 610 within the optical fiber experiences strain, the distance between the modulations of the refractive index for the FBG 610 may be altered due to the strain, and thus, the wavelength of light reflected by the FBG 610 will likewise be altered due to the change in distance between the modulations. Thus, the wavelength of the light reflected by the FBG 610 may proportional to the strain along the optical fiber 600 at a position of the FBG 610.

FBGs 610 inscribed in the optical fiber 600 can be used as robust axial strain sensors. The reflectivity spectrum of the FBG 610, when interrogated via spectral analysis redshifts under tension and blue-shifts under expansion. Thus, by positioning FBGs 610 at discrete locations along the length of the optical fiber 600 and using the optical fiber 600 as a pull wire, the system can interrogate local tension gradients by methods that include but are not limited to, e.g., optical frequency domain reflectometry, wavelength division multiplexing, etc.

In some embodiments, the optical fiber 600 can include multiple cores 605 and 607 within a single cladding 615. In such embodiments, each core 605 and 607 may operate as a separate optical path with sufficient distance and cladding 6015 separating the cores 605 and 607 such that the light traveling in each core 605 and 607 does not interact significantly with the light carried in other cores 605 and 607. In the embodiment of FIG. 25, a first core 605 is concentric with the cladding 615 and runs along a longitudinal axis of the optical fiber 600. A second core 607 branches from the first core 605 and runs parallel to the first core 605 along a portion of the optical fiber 600. For example, at the proximal end (e.g., the left side of FIG. 25) of the optical fiber 605 only the first core 605 is inscribed in the cladding 615 and the second core 607 is inscribed in the cladding 615 to branch from the first core 605 and run along the cladding 615 to the distal end of the optical fiber 600 (e.g., the right side of FIG. 25).

A plurality of FBGs may be inscribed in each core 605 and 607 of the optical fiber 600 at a plurality of locations along the length of the optical fiber 600. In some embodiments, each of the plurality of FBGs 610 can be configured to reflect light having a different frequency than the other FBGs 610. This can enable the system (e.g., the strain sensor 452 of FIG. 23 or one of the robotic medical systems 200, 300, or 400) to determine the strains at the locations of each of the FBGs 610 by determining the change from the expected frequencies of the reflected light. In some embodiments, the FBGs 610 are inscribed in the cores 605 and 607 at a regular period along the length of the optical fiber 600. For example, the length of each FBG may occupy 9 mm with a 1 mm spacing between the FBGs 610, thereby creating a periodicity of 10 mm along the cores 605 and 607. However, other FBG 610 lengths and spacings can be used in other embodiments. In some embodiments, a single FBG 610 may be formed as a continuous grating along the length of the core 605 (e.g., without spacings to separate the modulations into groups). The distance between modulations within the single FBG 610 may change along the length of the core 610 so that the system can determine the locations of strains measured along the optical fiber 600.

When the strain and shape analysis is applied to a multicore optical fiber 600, bending of the optical fiber 600 may induce strain on the cores 605 and 607 that can be measured by monitoring the wavelength shifts in each core 605 and 607. By having two or more cores 605 and 607 disposed off-axis in the optical fiber 600, bending of the optical fiber 600 induces different strains on each of the cores 605 and 607. These strains are a function of the local degree of bending of the optical fiber 600. For example, regions of the cores 605 and 607 containing the FBGs 610, if located at points where the optical fiber 600 is bent, can thereby be used to determine the amount of bending at those points. These data, combined with the known spacings of the FBGs 610, can be used to reconstruct the strain and/or shape of the optical fiber 600.

While aspects of this disclosure describe the use of FBGs, in other embodiments, an optical fiber can include slight imperfections that result in index of refraction variations along the fiber core. These variations can result in a small amount of backscatter that is called Rayleigh scatter. Changes in strain or temperature of the optical fiber cause changes to the effective length of the optical fiber. This change in the effective length results in variation or change of the spatial position of the Rayleigh scatter points. Cross correlation techniques can measure this change in the Rayleigh scattering and can extract information regarding the strain. These techniques can include using optical frequency domain reflectometer techniques in a manner that is very similar to that associated with low reflectivity fiber gratings. In some embodiment, the optical fiber pull wire can have a Rayleigh scattering probability which is augmented by inducing changes in the index of refraction of the optical fiber, which may be referred to herein as "enhanced Rayleigh scattering." Using such enhanced Rayleigh scattering augmentation may yield significantly higher signal to noise ratio for strain sensitivity over the inherent Rayleigh scattering of an optical fiber that is present due to natural properties of the optical fiber. Enhanced Rayleigh scattering may involve significant physical modification of what is otherwise an inherent property of the optical fiber. This modification can be performed happen post optical fiber manufacturing.

Methods and devices for calculating birefringence in an optical fiber based on Rayleigh scatter as well as apparatus and methods for measuring strain in an optical fiber using the spectral shift of Rayleigh scatter can be found in PCT Publication No. WO 2006/099056 filed on Mar. 9, 2006 and U.S. Pat. No. 6,545,760 filed on Mar. 24, 2000, both of which are fully incorporated herein by reference. Birefringence can be used to measure axial strain and/or temperature in a waveguide.

In some embodiments, enhanced Rayleigh scattering can be used in place of inscribed FBGs, and alternative interrogation methods may involve optical frequency domain reflectometry (e.g., using a monochromatic laser source, scanned and measured with a reference arm and an FBG/test arm) or wavelength division multiplexing techniques (wide spectrum source, reflectivity measured on spectrometer).

Figure 26:
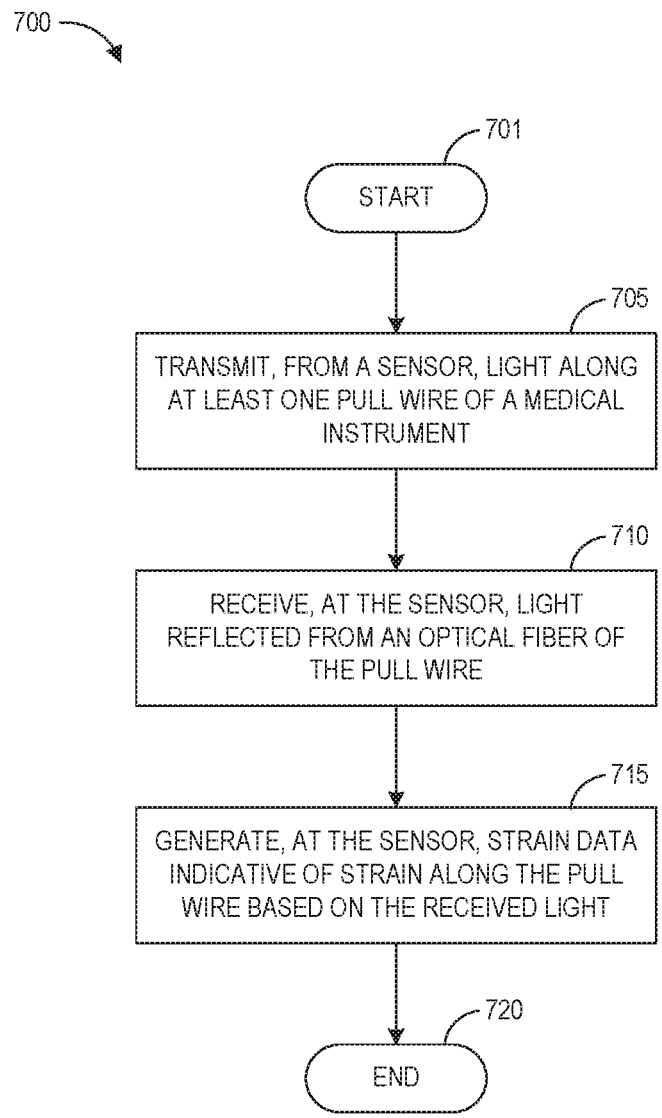
FIG. 26 is a flowchart illustrating an example method operable by a robotic system, or component(s) thereof, for sensing strain along a medical instrument in accordance with aspects of this disclosure.

FIG. 26 is a flowchart illustrating an example method operable by a robotic system, or component(s) thereof, for sensing strain along a medical instrument in accordance with aspects of this disclosure. For example, the steps of method 700 illustrated in FIG. 26 may be performed by one or more processor(s) and/or other component(s) of a medical robotic system (e.g., robotically-enabled system 10, or one of the robotic medical systems 200, 300, or 400) or associated system(s). For convenience, the method 700 is described as performed by the "system" in connection with the description of the method 700.

The method 700 begins at block 701. At block 705, the system transmits, from a sensor, light along at least one pull wire of the medical instrument. The sensor may include a strain sensor (e.g., the strain sensor 452) configured to transmit and receive light to/from an optical fiber. The pull wire may be included as part of a medical instrument including an elongate shaft. The pull wire may extend from a proximal end of the elongated shaft to a distal end of the elongated shaft and be configured to cause actuation of the medical instrument in at least one degree of freedom.

At block 710, the system receives, at the sensor, light reflected from the optical fiber of the pull wire. At block 715, the system generates, at the sensor, strain data indicative of strain along the pull wire based on the received light. In some embodiments, the optical fiber comprises at least one FBG inscribed therein and the FBG is configured to reflect light at a wavelength indicative of the strain along the pull wire at a position of the FBG. In some embodiments, the method 700 may further include the sensor transmitting the strain data to a processor. The processor may determine the strain at a position of the FBG along the pull wire based on the strain data. The processor may also be configured to determine a shape of the instrument based on the strain. The method 700 ends at block 720.

The method 700 may be used by the system to determine the strain along optical fibers included within a medical instrument. This strain data can be used in a number of different ways. For example, strain data can be analyzed to determine the shape of the optical fiber, and thus, the overall shape of the elongated shaft of a medical instrument in which the optical fiber is included. In some embodiments, the strain data may also be used as a technique to analyzing the viability of medical instrument design. For example, a prototype medical instrument may be fabricated with one or more optical fibers for pull wires. The prototype can be run through testing while analyzing the strains experiences by the optical fibers, for example, using method 700. The strains can then be analyzed to determine whether or not to adjust the design of the medical instrument. For example, if the strain at a particular location along the medical instrument is above a certain threshold, this may be an indication that a redesign to reduce the strain may be desirable.

B. Optical Connectors for Use with Optical Fiber Pull Wires.

Figure 27:
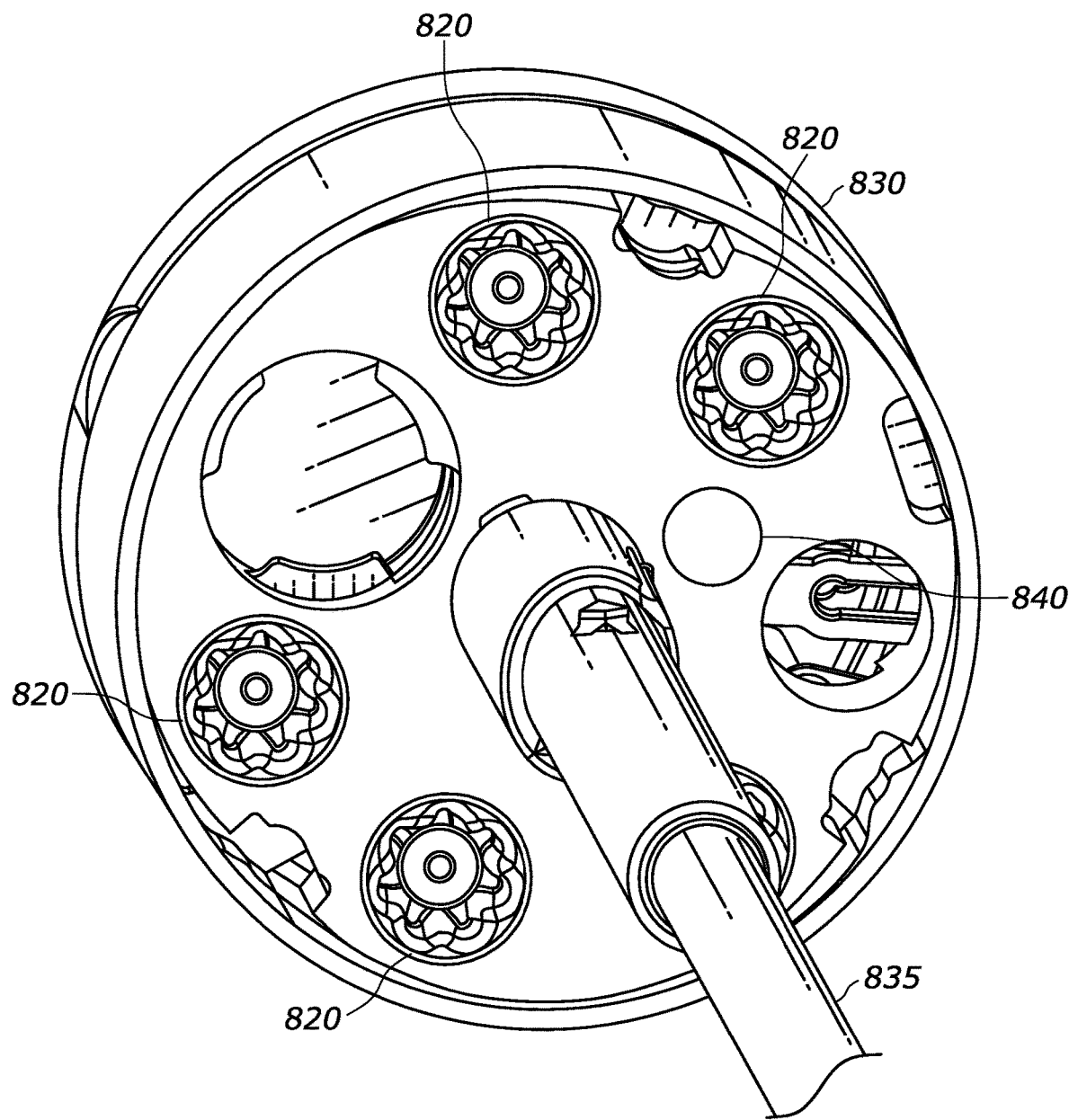
FIG. 27 illustrates an example view of an instrument base of a medical instrument in accordance with aspects of this disclosure.

FIG. 27 illustrates an example view of an instrument base 830 of a medical instrument 600 in accordance with aspects of this disclosure. In particular, the medical tool 600 includes the instrument base 830 from which an elongated shaft 835 extends. The instrument based 830 includes a plurality of inputs 820 (also referred to as drive inputs) which may be rotationally coupled to a plurality of spindles (such as spindles 520 of FIG. 24). In some embodiments, a strain sensor (e.g., the strain sensor 452 of FIG. 23) may not be included on the medical instrument 600 itself. Thus, the instrument base 830 may further include an optical connector 840 coupled to the optical fiber of the pull wire and configured to be coupled to an instrument driver. The optical fiber can be configured to be optically interrogated by light received from the optical connector 840 via the instrument driver. Although the optical connector 840 is illustrated as a single connector at a central locations, in other embodiments, each optical fiber may have a dedicated optical connector 840, which may be locate within the corresponding drive input 820. The optical connector 840 may include a separate port for each optical fiber pull wire included in the medical instrument, to provide a separate optical signal for each optical fiber.

Figure 28:
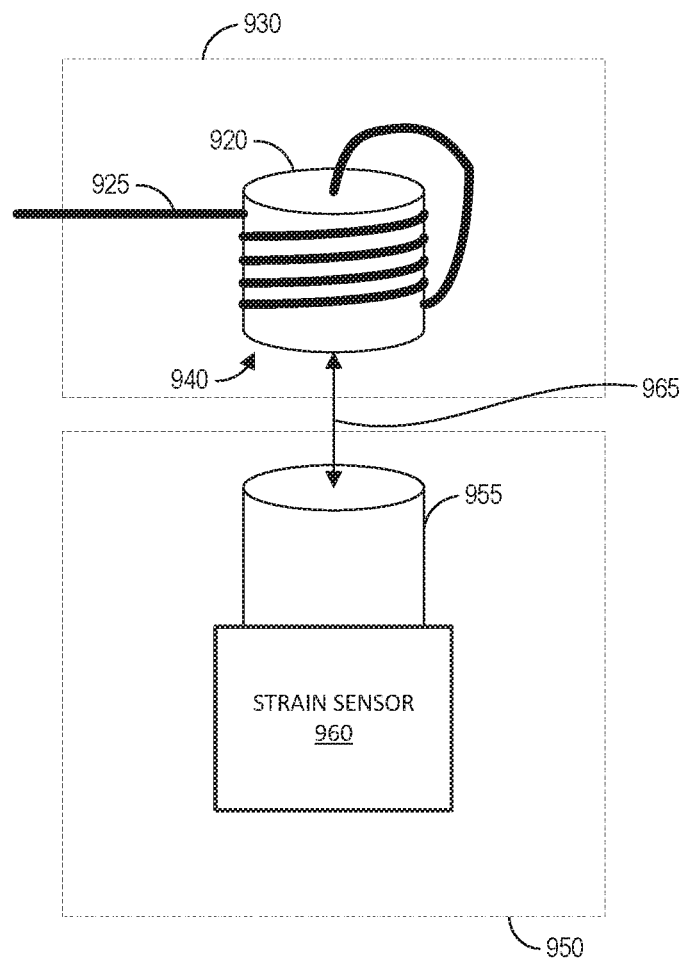
FIG. 28 illustrates an example view of the coupling of an instrument base to an instrument driver in accordance with aspects of this disclosure.

FIG. 28 illustrates an example view of the coupling of an instrument base 930 to an instrument driver 950 in accordance with aspects of this disclosure. In this embodiment, the instrument base 930 of a medical tool can be mechanically coupled to an instrument driver to receive torque from the instrument driver 950 to tension the optical fiber pull wires 925 of the medical instrument. The optical fiber 925 wraps around the spindle 920 which can be tensioned with rotation of a corresponding drive input (e.g., the drive input 820 of FIG. 27). The spindle 920 may also include an optical connector 940 formed on a bottom thereof which is formed within the drive input. A proximal end of the optical fiber 925 may be routed through the top of the spindle to be terminated at the optical connector 940.

The instrument driver 950 may also have an optical connector 955 configured to couple with the optical connector 940 of the instrument base 930. The instrument driver 950 may further include a strain sensor 960 configured to transmit light 965 to the optical fiber 925 and receive light 965 reflected from the optical fiber 925 via the optical connectors 940 and 955. The strain sensor 960 may further generate reflection spectrum data based on the wavelengths of light 965 reflected by the FBGs included in the optical fiber 925.

3. Implementing Systems and Terminology.

Implementations disclosed herein provide systems, methods and apparatus for sensing strain along a medical instrument.

It should be noted that the terms "couple," "coupling," "coupled" or other variations of the word couple as used herein may indicate either an indirect connection or a direct connection. For example, if a first component is "coupled" to a second component, the first component may be either indirectly connected to the second component via another component or directly connected to the second component.

The functions involved in sensing strain along medical instruments described herein may be stored as one or more instructions on a processor-readable or computer-readable medium. The term "computer-readable medium" refers to any available medium that can be accessed by a computer or processor. By way of example, and not limitation, such a medium may comprise random access memory (RAM), read-only memory (ROM), electrically erasable programmable read-only memory (EEPROM), flash memory, compact disc read-only memory (CD-ROM) or other optical disk storage, magnetic disk storage or other magnetic storage devices, or any other medium that can be used to store desired program code in the form of instructions or data structures and that can be accessed by a computer. It should be noted that a computer-readable medium may be tangible and non-transitory. As used herein, the term "code" may refer to software, instructions, code or data that is/are executable by a computing device or processor.

The methods disclosed herein comprise one or more steps or actions for achieving the described method. The method steps and/or actions may be interchanged with one another without departing from the scope of the claims. In other words, unless a specific order of steps or actions is required for proper operation of the method that is being described, the order and/or use of specific steps and/or actions may be modified without departing from the scope of the claims.

As used herein, the term "plurality" denotes two or more. For example, a plurality of components indicates two or more components. The term "determining" encompasses a wide variety of actions and, therefore, "determining" can include calculating, computing, processing, deriving, investigating, looking up (e.g., looking up in a table, a database or another data structure), ascertaining and the like. Also, "determining" can include receiving (e.g., receiving information), accessing (e.g., accessing data in a memory) and the like. Also, "determining" can include resolving, selecting, choosing, establishing and the like.

The phrase "based on" does not mean "based only on," unless expressly specified otherwise. In other words, the phrase "based on" describes both "based only on" and "based at least on."

The previous description of the disclosed implementations is provided to enable any person skilled in the art to make or use the present invention. Various modifications to these implementations will be readily apparent to those skilled in the art, and the generic principles defined herein may be applied to other implementations without departing from the scope of the invention. For example, it will be appreciated that one of ordinary skill in the art will be able to employ a number corresponding alternative and equivalent structural details, such as equivalent ways of fastening, mounting, coupling, or engaging tool components, equivalent mechanisms for producing particular actuation motions, and equivalent mechanisms for delivering electrical energy. Thus, the present invention is not intended to be limited to the implementations shown herein but is to be accorded the widest scope consistent with the principles and novel features disclosed herein.

What is claimed is:

1. A medical instrument, comprising:
    an elongated shaft; and
    at least one optical fiber pull wire extending from a proximal end of the elongated shaft to a distal end of the elongated shaft, the at least one optical fiber pull wire configured to cause actuation of the medical instrument in at least one degree of freedom,
    wherein the at least one optical fiber pull wire is configured to provide an indication of strain along the at least one optical fiber pull wire.

2. The medical instrument of claim 1, wherein:
    the at least one optical fiber pull wire comprises at least one Fiber Bragg Grating (FBG) inscribed therein, and
    the FBG is configured to reflect light at a wavelength indicative of the strain along the at least one optical fiber pull wire at a position of the FBG.

3. The medical instrument of claim 2, wherein the wavelength of the light reflected by the FBG is proportional to the strain along the at least one optical fiber pull wire at the position of the FBG.

4. The medical instrument of claim 2, wherein the at least one optical fiber pull wire comprises a core and a cladding surrounding the core, wherein the at least one FBG is inscribed in the core.

5. The medical instrument of claim 4, wherein the at least one optical fiber pull wire further comprises a coating surrounding the cladding.

6. The medical instrument of claim 2, wherein:
    the at least one optical fiber pull wire comprises a cladding and a plurality of cores located within the cladding,
    a first one of the cores is concentric with the cladding,
    each of the remaining cores branch from the first core and run parallel to the first core along a portion of the at least one optical fiber pull wire, and
    each of the plurality of cores is inscribed with the at least one FBG.

7. The medical instrument of claim 2, wherein the at least one FBG comprises a plurality of FBGs inscribed in the at least one optical fiber pull wire at a plurality of locations along a length of the at least one optical fiber pull wire.

8. The medical instrument of claim 7, wherein each of the plurality of FBGs is configured to reflect light having a different frequency than the other FBGs of the plurality.

9. The medical instrument of claim 7, wherein the plurality of FBGs are inscribed in the at least one optical fiber pull wire at a regular period along the length of the at least one optical fiber pull wire.

10. The medical instrument of claim 2, wherein the at least one FBG forms a continuous grating along a length of the at least one optical fiber pull wire.

11. The medical instrument of claim 1, further comprising:
    an optical connector coupled to the at least one optical fiber pull wire and configured to couple to an instrument driver,
    wherein the at least one optical fiber pull wire is configured to be optically interrogated by light received from the optical connector via the instrument driver.

12. The medical instrument of claim 1, wherein the at least one optical fiber pull wire comprises a plurality of pull wires, each of the plurality of pull wires configured to actuate the medical instrument in a separate degree of freedom relative to at least one of the other pull wires of the plurality.

13. The medical instrument of claim 1, wherein a Rayleigh scattering probability of the at least one optical fiber pull wire is augmented by inducing changes in an index of refraction of the at least one optical fiber pull wire.

14. The medical instrument of claim 1, further comprising:
    an end effector at a distal end of the elongated shaft, the end effector configured to be actuated by the at least one optical fiber pull wire.

15. A medical robotic system, comprising:
a medical instrument configured to be inserted into a region of a body, the medical instrument comprising:
an elongated shaft,
at least one optical fiber pull wire extending from a proximal end of the elongated shaft to a distal end of the elongated shaft, the at least one optical fiber pull wire configured to cause actuation of the medical instrument in at least one degree of freedom, wherein the at least one optical fiber pull wire is configured to provide an indication of strain along the pull wire;
a sensor configured to generate strain data indicative of the strain along the at least one optical fiber pull wire; and
an instrument positioning device configured to be attached to the instrument and control movement of the instrument via actuation of the at least one optical fiber pull wire.

16. The system of claim 15, wherein:
the at least one optical fiber pull wire comprises at least one Fiber Bragg Grating (FBG) inscribed therein, and
the FBG is configured to reflect light at a wavelength indicative of the strain along the at least one optical fiber pull wire at a position of the FBG.

17. The system of claim 16, wherein the wavelength of the light reflected by the FBG is proportional to the strain along the at least one optical fiber pull wire at the position of the FBG.

18. The system of claim 16, further comprising:
at least one computer-readable memory having stored thereon executable instructions; and
one or more processors in communication with the at least one computer-readable memory and configured to execute the instructions to cause the system to at least:
receive the strain data from the sensor; and
determine the strain at the position of the FBG along the at least one optical fiber pull wire based on the strain data.

19. The system of claim 18, wherein the instructions, when executed, further cause the system to:
determine a shape of the instrument based on the strain.

20. The system of claim 16, wherein the at least one optical fiber pull wire comprises a core and a cladding surrounding the core, wherein the at least one FBG is inscribed in the core.

21. The system of claim 20, wherein the at least one optical fiber pull wire further comprises a coating surrounding the cladding.

22. The system of claim 16, wherein:
the at least one optical fiber pull wire comprises a cladding and a plurality of cores located within the cladding,
a first one of the cores is concentric with the cladding,
each of the remaining cores branch from the first core and run parallel to the first core along a portion of the at least one optical fiber pull wire, and
each of the plurality of cores is inscribed with the at least one FBG.

23. The system of claim 16, wherein the at least one FBG comprises a plurality of FBGs inscribed in the at least one optical fiber pull wire at a plurality of locations along a length of the at least one optical fiber pull wire.

24. The system of claim 23, wherein each of the plurality of FBGs is configured to reflect light having a different frequency than the other FBGs of the plurality.

25. The system of claim 23, wherein the plurality of FBGs are inscribed in the at least one optical fiber pull wire at a regular period along the length of the optical fiber.

26. The system of claim 16, wherein the at least one FBG forms a continuous grating along a length of the at least one optical fiber pull wire.

27. The system of claim 15, wherein:
the medical instrument further comprises an optical connector coupled to the at least one optical fiber pull wire and configured to couple to the instrument positioning device, and
the at least one optical fiber pull wire is configured to be optically interrogated by light received from the optical connector via the instrument positioning device.

28. The system of claim 15, wherein the at least one optical fiber pull wire comprises a plurality of pull wires, each of the plurality of pull wires configured to actuate the medical instrument in a separate degree of freedom relative to at least one of the other pull wires of the plurality.

29. The system of claim 15, wherein a Rayleigh scattering probability of the at least one optical fiber pull wire is augmented by inducing changes in an index of refraction of the at least one optical fiber pull wire.

30. The system of claim 15, wherein the medical instrument
further comprises:
an end effector at a distal end of the elongated shaft, the end effector configured to be actuated by the at least one optical fiber pull wire.

* * * * *